United States Patent [19]

Leach et al.

[11] Patent Number: 4,555,930

[45] Date of Patent: Dec. 3, 1985

[54] DIGITAL GAS SENSING SYSTEM

[75] Inventors: Thomas W. Leach, Waldwick; James Schaeffer, North Caldwell, both of N.J.

[73] Assignee: Control Instruments Corp., Fairfield, N.J.

[21] Appl. No.: 580,028

[22] Filed: Feb. 14, 1984

[51] Int. Cl.[4] ............................................. G01N 31/00
[52] U.S. Cl. ............................................. 73/23; 73/16
[58] Field of Search ..................... 73/23, 27 R, 1 G; 340/534, 538, 632, 633, 634; 364/497, 498, 499; 422/94, 98; 204/406, 401

[56] References Cited

U.S. PATENT DOCUMENTS

| | | | |
|---|---|---|---|
| 3,481,179 | 12/1969 | Howarth | 73/23 |
| 3,710,372 | 1/1973 | Andersson et al. | 340/517 |
| 4,151,738 | 5/1979 | Hyer et al. | 73/1 G |
| 4,290,055 | 9/1981 | Furney et al. | 340/518 |
| 4,305,724 | 12/1981 | Micko | 73/27 R |
| 4,359,721 | 11/1982 | Galvin et al. | 340/525 |
| 4,384,925 | 5/1983 | Stetter et al. | 422/98 |
| 4,388,822 | 6/1983 | Heller | 73/23 |
| 4,390,869 | 6/1983 | Christen et al. | 340/632 |
| 4,422,073 | 12/1983 | Winner | 340/632 |
| 4,464,653 | 8/1984 | Winner | 422/94 |

Primary Examiner—Stephen A. Kreitman
Attorney, Agent, or Firm—Richard C. Woodbridge

[57] ABSTRACT

A digital gas sensing system comprises a plurality of satellite subassembly units each including a central processing unit (CPU) and a plurality of "intelligent" sensors connected to the satellite subassembly units by a single pair of leads. The satellite subassembly units communicate to the sensors in a code having a predetermined number of digital bits. Each sensor has internal "intelligence" and recognizes its own unique address and responds to the satellite subassembly unit in a predetermined code that varies from the satellite subassembly unit code by one parity bit. This arrangement makes it possible for other sensors to distinguish between transmissions from the satellite subassembly unit and transmissions from other sensors. The net result is that the system is able to operate very reliably using only two leads to connect all of the sensors to the satellite sub subassembly unit thereby greatly reducing the wiring and installation costs of the system. To further expand the potential of the system it is also possible to link a plurality of satellite subassembly units together to a single master control unit.

11 Claims, 19 Drawing Figures

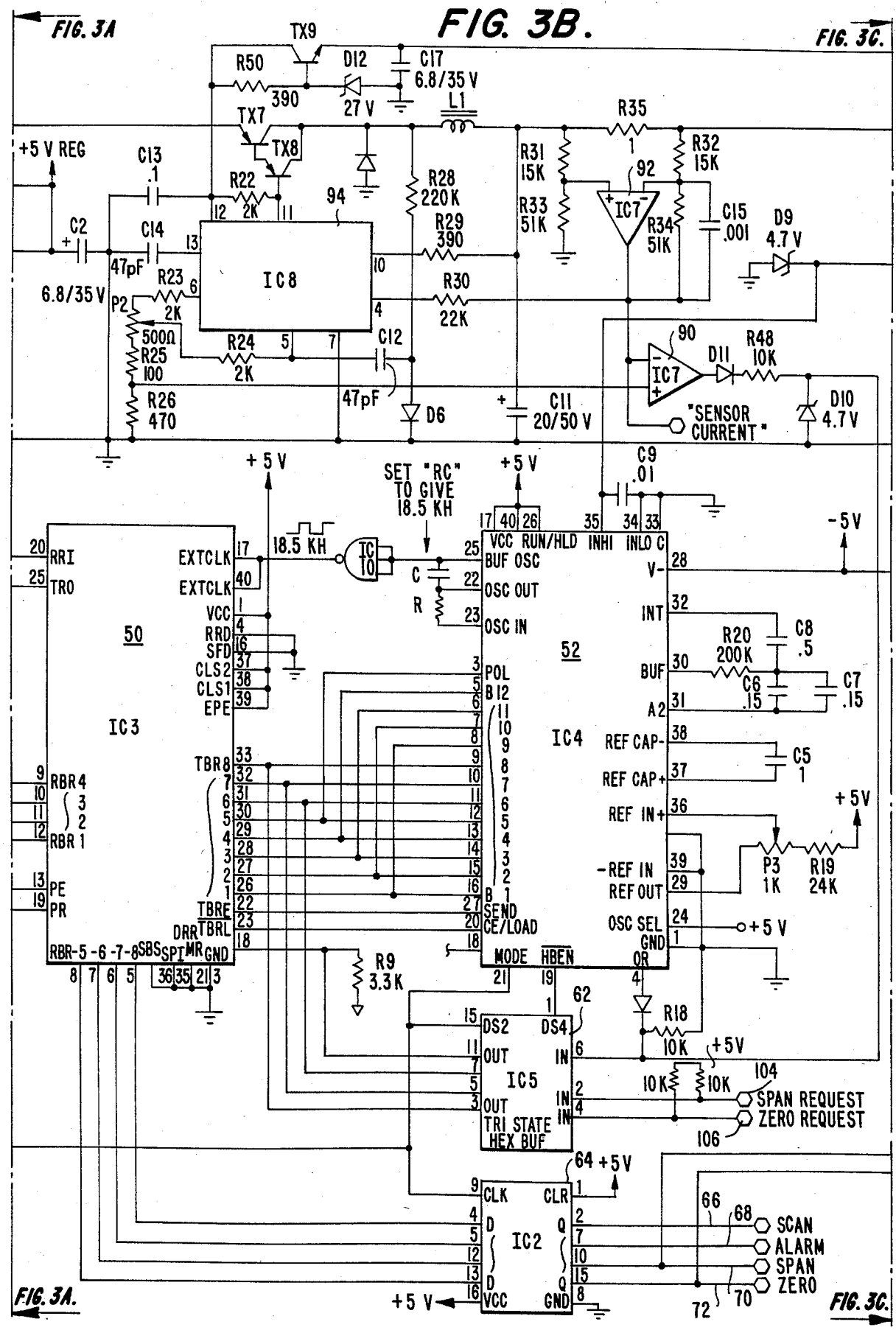

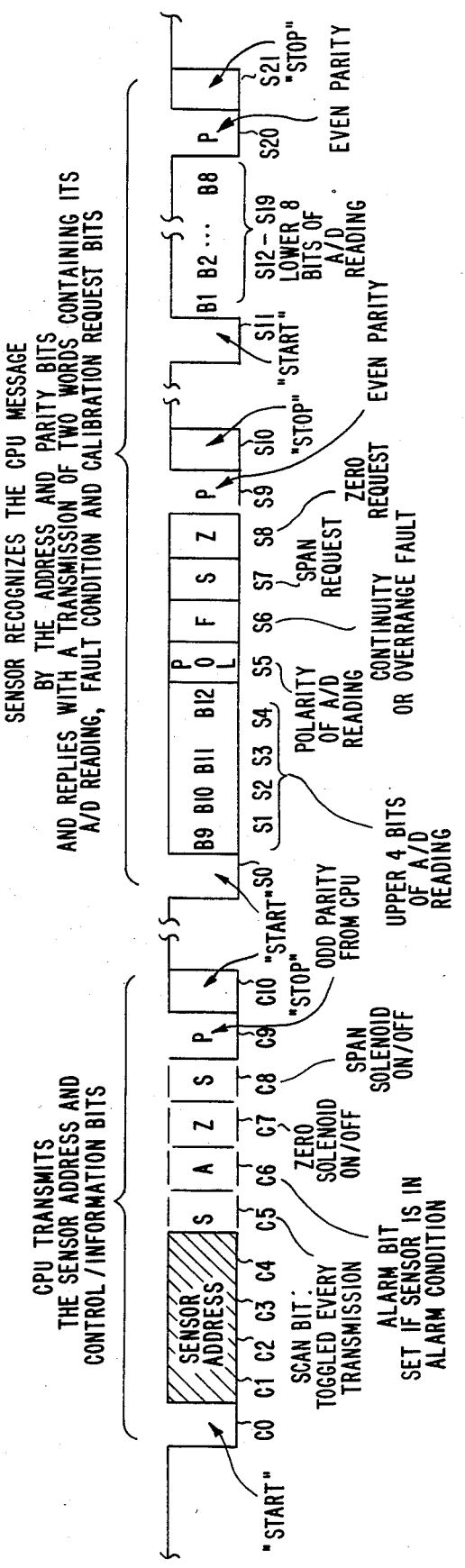

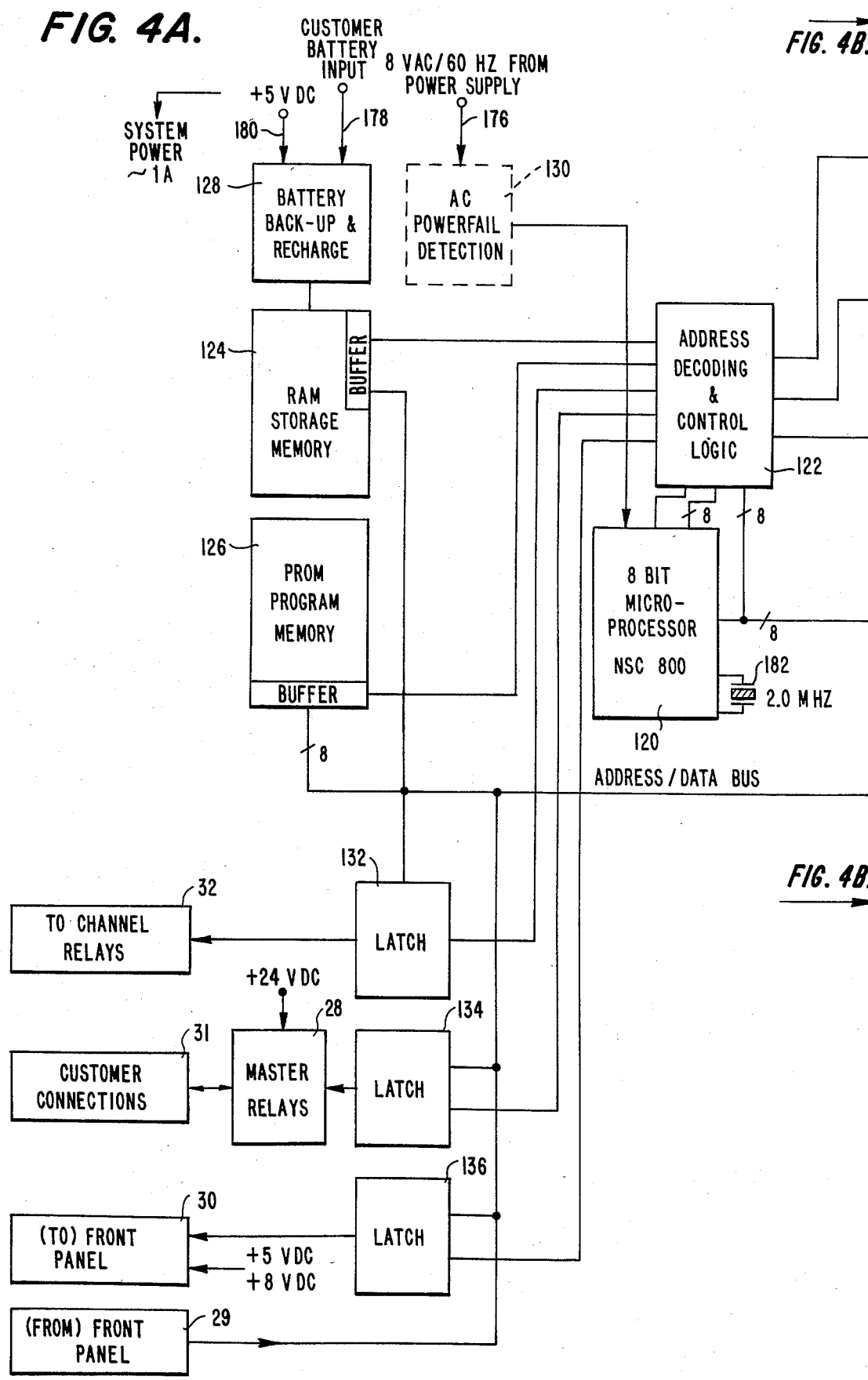

DIGITAL GAS SENSING SYSTEM

BACKGROUND OF THE INVENTION

1. Field of the Invention

This invention relates to a system for automatically monitoring gas sensors from a central location.

2. Description of the Prior Art

Industry has relied on gas detectors for the protection of life and property. Gas detectors typically use remote sensors operating on the principal of diffusion so that the presence of any hazardous gas, flammable or toxic, may quickly be detected at a remote location of a facility or process. The presence of such gas is reported to a control room. The concentration of the gas is reported and an alarm is activated when the concentration exceeds certain preset values.

Conventional prior art sensors are individually wired to the field location from the central control panel with whatever number of wires are required to deliver the power and return the information. This is usually a minimum of three to five wires for each sensor.

The major problem in any detection and alarm system is reliability. To be safe the operator must frequently check and calibrate each sensor. Calibration must be done quite frequently in order to assure reliability. For hazardous vapors the standard in the industry is catalytic combustion. Such sensors are known to loose their ability to detect flammable vapors over time and therefore become insensitive to the presence of hazardous gas and fail to produce an adequate alarm at the central monitoring panel.

A number of attempts have been made to reduce the number of wires connecting the sensors in the field and to control the cost of installation.

It is possible to employ multiple wires to each remote sensor to deliver the various electrical instructions that are required to calibrate a sensor from a central monitor panel. Such multiplex wire systems control all the various functions of zero, span, power and signal return. An operator manipulates all the functions from a central panel and knows if a particular sensor is accurate and reliable. Usually the system is calibrated by two people. One operator provides the sensor with a test gas and another operator at the central panel notes the reading and makes the appropriate adjustment. This arrangement produces acceptable reliability if it is done frequently enough. Many users fail to make calibrations frequent enough to detect sensor calibration problems. In order to reduce the cost of manpower for calibration purposes, various instruments have been developed so that equipment may be calibrated by one man.

There are several different types of sensing systems disclosed in the prior art literature. Such systems are found in the patent literature as well as in general commercial literature. The following prior art devices and systems appear to be relevant and typical of that prior art.

U.S. Pat. No. 4,388,822 discloses a microprocessor controlled gas detector system which requires three wires to function. A probe converts the signals from analog to digital ratiometric and is responsive to a reset pulse generated by the microprocessor. The reference discloses that it is known to use a microprocessor to control a probe which produces a signal in response to the detection of a gas.

U.S. Pat. No. 4,390,869 discloses a gas detection system in which a plurality of sensing units are connected together in parallel. This appears to be a four wire type system. The sensing units can be grouped in various different ways to obtain various different gas detection alarm data. Moreover, the sensors are arranged so that a malfunction in the unit itself can be signalled to a central station.

U.S. Pat. No. 4,290,055 is of general interest in that it discloses a detector system, primarily for fire, connected by two pair of wires. The wire carrying the interrogatory pulse to each detector is connected serially to said detectors. U.S. Pat. No. 4,290,055 is not directed towards gas detection. However, it is of some relevance in that it teaches sequential sampling of serially connected detection stations by a scanning mechanism.

U.S. Pat. Nos. 3,710,372 and 4,359,721 disclose serially connected detection systems wired to allow the sensing of individual detector units. For example, U.S. Pat. No. 4,359,721 discloses a system in which a frequency divider provides for time sampling of a serially connected sensor. The output is demodulated in order to detect the values sensed by the sensors.

U.S. Pat. No. 4,384,925 is of interest in that it teaches a microprocessor controlled gas sensing system which automatically controls a solenoid valve to feed a standard calibration gas to a sensor at preset levels.

Similarly, U.S. Pat. No. 4,151,738 discloses another automatic gas calibration system. A zero gas is sampled continuously except during sampling or recalibration operation and a standard gas is sampled periodically and automatically during the recalibration mode.

U.S. Pat. No. 3,481,179 is of interest only in that it discloses a gas detection sensor head with an annular channel around the sensor for feeding and calibration gas. The device further includes a means for evenly distributing radial flow of calibration gas. This device comprises a sintered bronze ring which resists the gas flow.

U.S. Pat. No. 4,305,724 is assigned to Delphian Partners. Delphian Partners is known to use a computer type instrument. The sensors are typically analog in that they transmit analog signal to a computer using a four-20 milliamp proportional signal. Calibration is done in the field by signalling from the sensor to the CPU with a magnetic type switch. The sensor contains no intelligence, but the computer does take the information of "zero" and "span" generated by the man in the field so that the computer ends up with "zero" and a "span" number which it can use to compute a reading. The operator in the field has to manually connect or cover the sensor to introduce the test gases and he also has to manually operate a magnetic device referred to by Delphian as a "Sensical" in order to make the system work properly.

The Bendix Corporation employs a two wire sensing device including two wires to carry power. On the power wires it communicates the information about the sensors using a high frequency carrier. The carrier is modulated with coded sensor information. In order to calibrate the sensor the operator in the control room sets the module in the calibrate mode. At the sensor, zero and test gases must be added by the operator in the field. The microprocessor knows to hold the peak reading because the operator pushes a button on the sensor synchronizing the reading with the test gas. The value of the test gas is digitally entered into the module and the sensor peak signal is calibrated to the test value.

Returning the module to normal establishes the new calibration. Accordingly, two men are required to operate and calibrate the system or one man traveling to and from the control room to the sensor. Insofar as understood the Bendix system does not provide for the transmission back and forth of intelligence between the control module and the sensor. Each sensor is wired individually to the control unit.

International Sensor Technology offers a system that requires the operator to initiate testing so that the computer will adjust the "zero" and the "span" settings. The sensor can be calibrated by a man in the field or remotely through a sample tube. The system only uses the sample tube for calibration gas. Each sensor is analog and therefore transmits an analog 4–20 milliamp signal to the central control unit. There appears to be no intelligent communication between the sensor and the control section. The computer is basically a data logger with the ability to digitize the information from the sensors.

Rexnard has a multichannel unit that sequences eight sensors. Each sensor is connected by a series of wire. The information is transmitted by a voltage-to-frequency method. All sensors contain a "zero" and "span" mechanism. They are field calibrated by opening the explosion proof housing, plugging a meter into it, introducing the "zero" and the "test" gases and making the appropriate adjustments at the sensor.

Honeywell, Inc. has a differential transmitter known as the ST3000 Smart Transmitter which may be used in the field to remotely configure, re-range, diagnose and display process values. The device is primarily intended to measure and control process flow, liquid level and pressures in a system. The device is unusual in that it can be inserted at any place within the circuit loop and interrogate remote sensors at any location within that loop. However, the device appears to be otherwise unrelated to the hazardous gas sensor of the present invention.

MSA Instruments has an instrument known as the DAN ™ 6000 Data Acquisition Network for sensing combustible gas at remote locations. The device is capable of turning on a zero and span gas in the field. Calibration is done in the field by an operator who uses a magnet to trigger the calibration procedure. The procedure is a timed sequence-zero and then span gas. If the results of the calibrations are within the time window and if the deviation is ±10% then the device automatically corrects itself and prints out the values. If the results are outside of the ±10% value then the device must be corrected by the man in the field. The device can accomodate up to 14 remote station monitors with up to 16 sensors each. MSA also provides a calibration check kit including two three liter cans of gas, a balloon designed to hold one-half liter of gas, and the appropriate connections and clamps for introducing the gas to the detectors. The manual procedure necessary for testing the sensor appears to be relatively complicated and requires the presence of an individual in the field under possibly hazardous conditions.

Insofar as understood, none of the prior art systems teach a simple digital two wire mechanism for reliably connecting sensors to a control unit. The system disclosed herein is a true digital system which has extreme reliability because of its unique method of operation.

SUMMARY OF THE INVENTION

Briefly described the invention comprises a gas detection system for connecting up to sixteen sensors to a satellite subassembly unit including a CPU by a single twisted pair of wires. A group of satellites can also be connected to a master computer which allows the ultimate system to control an indefinite number of sensors. Each satellite unit talks to its sixteen sensors in digital words. Each sensor recognizes its own unique address and responds back to the satellite unit with a digital answer. The method by which the satellite unit and the digital sensors correspond with each other is not conventional in this context. The satellite unit addresses each sensor in a digital code. If a particular sensor is addressed it responds with a code that differs from the satellite unit code by one parity bit. Therefore, the satellite unit will recognize when a particular sensor responds, but the other sensors will not respond to the answer of the addressed sensor. This technique maximizes the data that can be transmitted between the satellite unit and the sensor and provides for a much more reliable system while taking advantage of the parity bit function built into the microprocessors employed in the system. The satellite unit can address a sensor and command that a "zero" solenoid be turned on which will allow compressed air to be directed into the diffusion sensor element. The value of the electrical signal generated is then sent back digitally to the satellite unit CPU where it is stored. The sensor then is directed to turn on the "span" solenoid and the calibration gas (span gas) is then directed into the sensor element. The digital output of the sensor is then received by the satellite unit CPU and stored. The CPU then computes the value of the calibration gas in terms of percent of scale. Values of samples of unknown gases can be computed by extrapolating from the zero and span gas readings.

The zero and span calibration routine can be initiated from the control panel or at the sensor or automatically by the satellite unit CPU on a time sequence basis. By a push of the button the operator is capable of checking out and calibrating each instrument per channel. Alternatively, the system can be checked out by groups of sensors or the system can automatically check and calibrate itself without the assistance of an operator. Should any channel fail to calibrate correctly, the system will indicate the defective sensor. Therefore, the system can identify malfunctioning sensors and discriminate between those that are accurate and functioning and those that are malfunctioning. Because the sensors are frequently used in areas where hazardous gases are present it is highly desirable not to have a man in the field each time that a sensor has to be checked out.

These and other features of the invention will be more readily undestood by referring to the following drawings.

BRIEF DESCRIPTION OF THE DRAWINGS

FIGS. 3A–3C illustrate a typical digital sensor unit.

FIG. 3E illustrates a typical transmission of digital data bits between the satellite unit and typical sensor unit.

FIGS. 4A-4B illustrate a typical satellite subassembly unit in functional block diagram form.

DETAILED DESCRIPTION OF THE PREFERRED EMBODIMENT

During the course of this description like numbers will be used to identify like elements according to the different figures that illustrate the invention.

Figure 1:
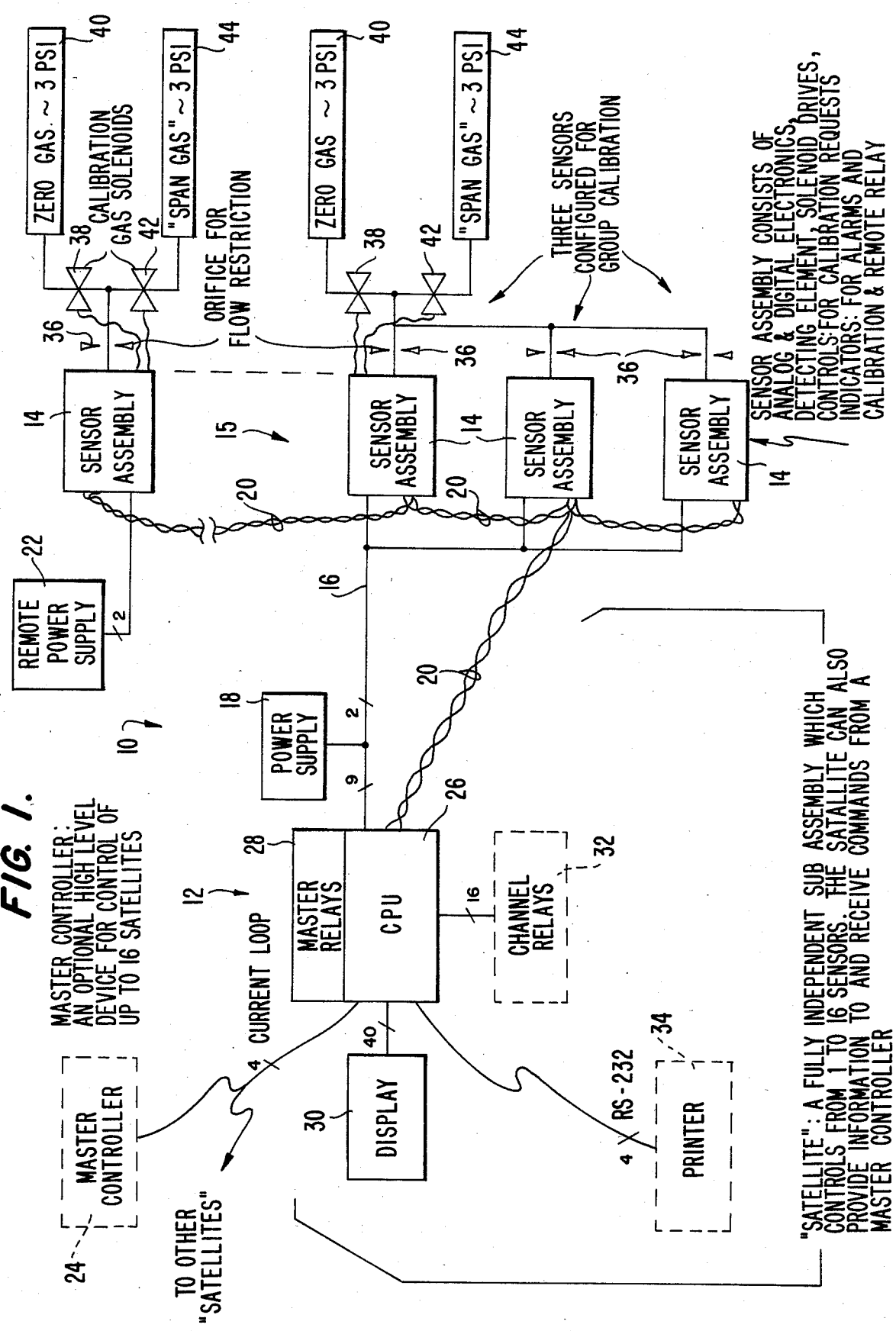
FIG. 1 is a functional block schematic diagram of the gas sensing system according to the preferred embodiment of the invention.

FIG. 1 is a functional block diagram of the entire gas detection system. The major elements comprise a satellite subassembly unit 12 connected to a plurality of sensors 15 by a single pair of wires 20. Power is supplied to the satellite subassembly unit 12 and the sensor assemblies 14 by a power supply 18 over power lines 16. A remote power supply 22 can also be used to supply power to sensor assemblies 14 in remote locations. The heart of the satellite subassembly 12 comprises the CPU 26 itself and a set of master relays 28 and a set of channel relays 32. CPU 26 controls peripheral display 30 and printer 34.

Satellite subassembly 12 comprises a self-contained unit which may be controlled by a master controller 24. Each satellite subassembly 12 can control from between 1 to 16 sensors 15. Satellite 12 can provide information to and receive commands from the master controller 24. A single master controller 24 can control many satellite subassemblies 12 each of which can control up to 16 sensors 15 a piece. Therefore, by tying all the satellite subassemblies 12 into a single master controller 24 it is possible to control a large number of sensors 15.

Each sensor unit 15 includes a sensor assembly 14 connected to a source of "zero gas" 40 and a source of "span gas" 44. The zero gas 40 is metered through a solenoid valve 38 into the sensor elements 81 and 83 in sensor assembly 14. Similarly, the span gas 44 is metered through a solenoid valve 42 into sensor assembly 14. An orifice 36 acts as a flow restrictor for the gases entering sensor assembly 14. The zero gas and span gas are preferably introduced at pressures of approximately 3 lbs. per square inch. Each sensor assembly 14 consists of analog and digital electronics, detecting elements, solenoid drives, controls for calibration requests, indicators for alarms and calibrations and remote relays. The internal structure of sensor assemblies 14 are illustrated in greater detail in FIGS. 3A-3D.

Figure 2:
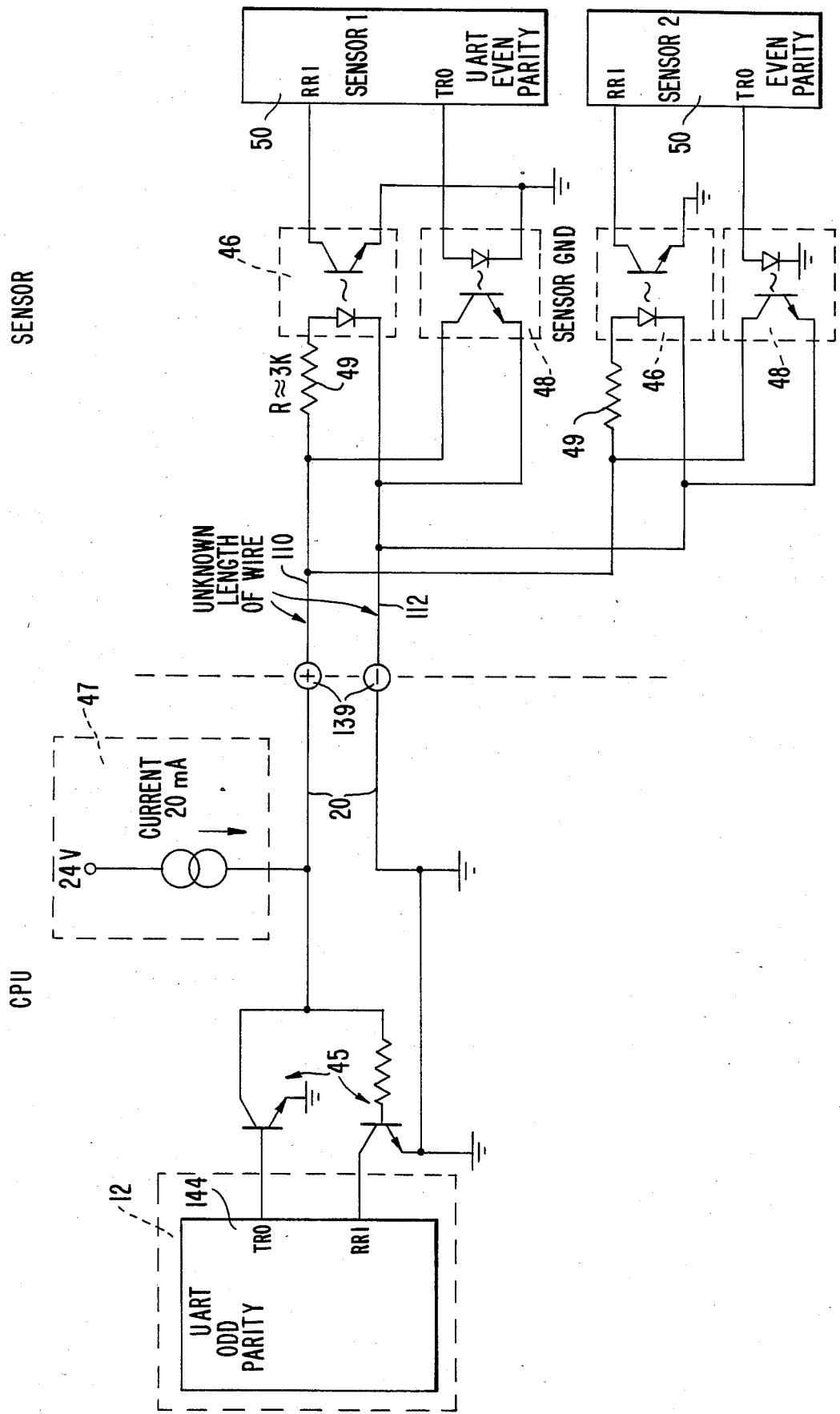
FIG. 2 is a detailed drawing illustrating the coupling mechanism between the satellite subassembly unit and the sensors.
Figure 3A:
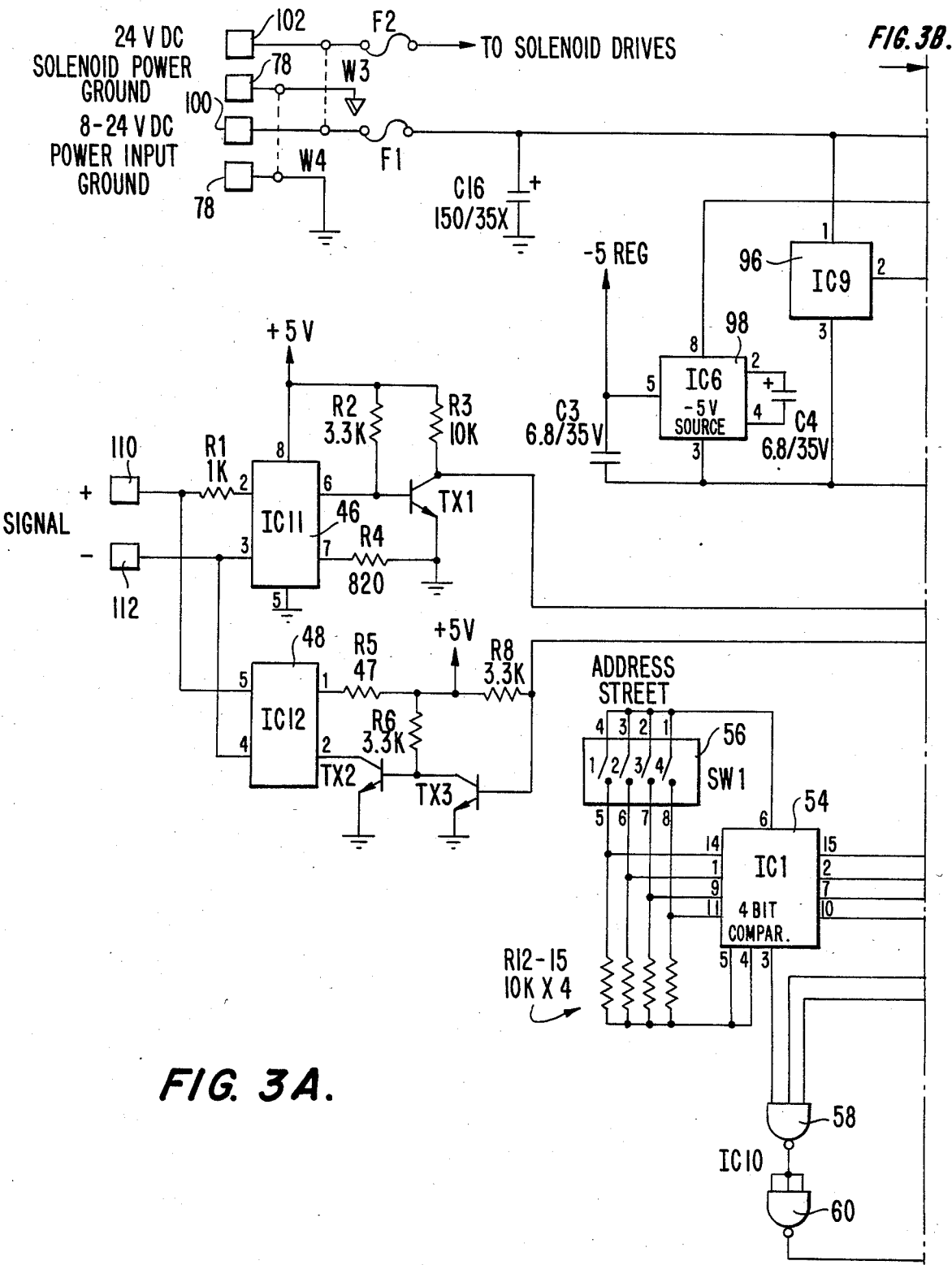
Figure 3C:
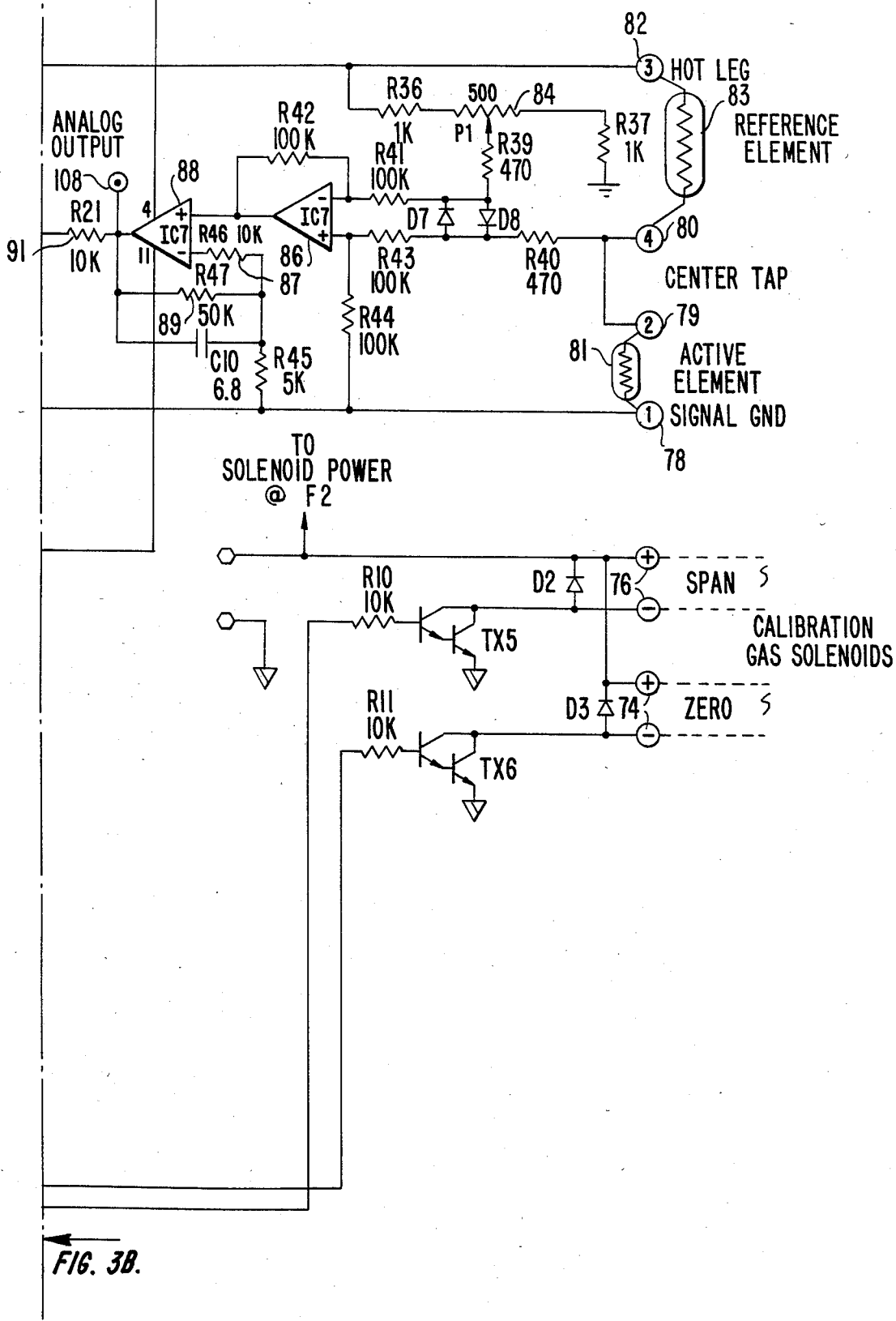
Figure 3D:
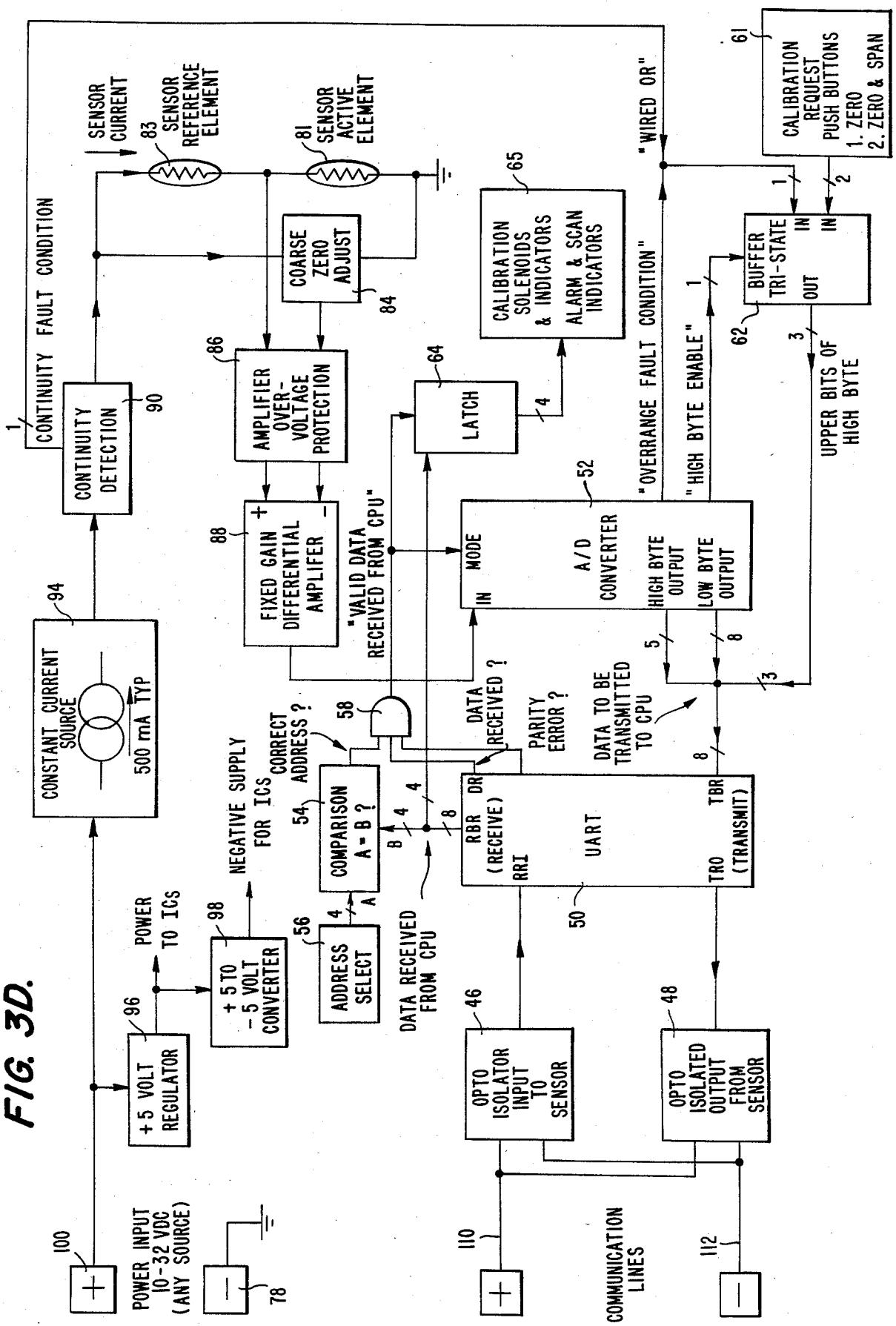
FIG. 3D is a schematic of the sensor unit of FIGS. 3A–3C illustrated in functional block diagram form.

FIG. 2 illustrates the transmission system between the satellite subassembly 12 and the sensor assembly 14. Internal sensor UART 144 of satellite subassembly 12 transmits and receives signals from sensor assembly 14 through a current loop half duplex interface 138 and drive transistors 45. A 20 milliampere current source 47 provides power to data lines 110 and 112 which are collectively referred to as a pair of data wires 20. The connection terminals 139 illustrated in FIG. 2 is the point at which the leads from the satellite subassembly 12 are connected to the leads of the sensor assemblies 14.

Each sensor assembly 14 includes a read-in LED/phototransistor coupler 46 and a read-out LED/phototransistor coupler 48. A 3K ohm ballast resistor 49 serves to limit the current flowing through data leads 110 and 112. The structure of photocouplers 46 and 48 is well known to those of ordinary skill in the art and serves to electrically isolate the satellite subassemblies 12 from the sensor assemblies 14. The output of the read-in photocoupler 46 is attached to the read port RI of sensor UART 50. Similarly, the transmit output lead TR0 of sensor UART 50 is attached to the read-out photocoupler 48.

In summary the satellite subassembly UART 144 generates digital words of odd parity and transmits them over line 110 and through photocoupler 46 to the read input RRI of sensor 50 of the sensor assembly 14. Conversely, the sensor UART 50 produces digital words having even parity and transmits them through photocoupler 48 and data line 112 to the read-input RRI of the satellite subassembly UART 144. The odd/even parity transmission mode of the invention makes it possible to efficiently connect a plurality of sensors 15 to a satellite subassembly 12.

Details of the operation of the sensor units 15 can be more fully understood by reference to FIGS. 3A-3E. As previously described, incoming signals from the satellite assembly 12 pass through line 110, photocoupler 46 and into the read terminal RR1 of sensor UART 50. Transmissions from UART 50 pass from port TR0 to photocoupler 48 and output line 112. While the invention has been described in terms of electrically conductive lines 110 and 112, it will be understood by those of ordinary skill in the art that fiberoptic fibers may be used in place of electrically conductive leads instead.

During typical operation the satellite subassembly 14 will transmit a digital code having odd parity as represented by digital bits C0 through C10 of FIG. 3E. The digital bits C0 through C10 have the following logic definitions:

C0—the "start bit"
C1 through C4—a four bit sensor address code
C5—the "scan bit"—toggled every transmission
C6—the "alarm bit"—set if the sensor is in the alarm condition
C7—the "zero solenoid on/off" bit
C8—the "span solenoid on/off" bit
C9—the odd "parity" bit from the CPU 26
C10—a "stop" bit Every sensor 15 has a different four digit address code repreented by data bits C1-C4. Each sensor 15 recognizes the CPU message by its unique sensor address and the odd parity bit and replies with a transmission of two words which contain its analog/digital (A/D) reading, fault conditions, and calibration and request bits. An important aspect of the invention is that a sensor 15 will respond with an even parity bit if the CPU transmits with an odd parity bit. A typical two word sensor response includes data bits S0 through S21 which have the following logical definitions:

S0—the sensor "start" bit

S1 through S4—the upper four bits of the A/D reading
S5—the polarity of the A/D reading
S6—The continuity or overrange fault bit
S7—the "span" gas request
S8—the "zero" gas request
S9—the "even" parity bit
S10—the "stop bit After a pause the second word is transmitted which includes the following data bits:
S11—the "start" bit
S12-S19—the lower eight bits of the A/D reading
S20—a second sensor "even" parity bit
S21—the "stop" bit During a typical transmission from the satellite subassembly 14 the CPU word (C0–C10) is fed into the RRI port of sensor UART 50. After the CPU transmission is received by UART 50, the four bit address portion (C1–C4) is compared in comparator 54 with the address of that particular sensor. The sensor address is selected by a four bit address select circuit 56. If the address transmitted by the CPU 26 is the same as the address selected by the address select circuit 56, then comparator 54 produces an output to the input of NAND circuit 58. NAND gate 58 has a second and third input PE and DR respectively from sensor UART 50. The DR input is the data received input. The PE input is the parity error input. NAND gate 58 does not produce an output unless the sensor 15 is correctly addressed and there is a parity error (indicating a CPU transmission) and if the data is ready. The output from NAND gate 58 is fed through inverter 60 and acts as an input to analog to digital converter 52, and the quad D flip-flop latch circuit 64. Latch circuit 64 produces the following four outputs: Scan 66, Alarm 68, Span 70 and Zero 72. Span lead 70 is connected through driver transistor pair TX5 and produces an output across Span terminals 76 to initiate span gas to a sensor cell. Similarly, Zero output terminal 72 is connected through driver transistor pair TX6 to zero gas terminals 74. An output will appear across the Zero Gas Terminal 74 if a zero bit "Z" is present at position C7 in the transmission train. Similarly a signal will appear across terminal 76 calling for span gas if a span gas bit "S" is present at position C8 in the transmission train from the CPU 26.

The Zero Gas preferably comprises an uncontaminated source of air. The span gas preferably comprises 2% hydrogen which is the industry standard for 50% of the acceptable lower flammable limit (LFL). Span Gas Terminal 76 and Zero Gas Terminals 74 are attached to solenoids 38 and 42 respectively as illustrated in FIG. 1 for the purpose of applying the Span Gas or Zero Gas as required.

Signals from the sensor itself are applied to terminals 78, 79, 80 and 82. Terminal 78 comprises a common signal ground. Terminal 79 and 80 comprise the center top of the sensor and terminal 82 is connected to the hot leg of the sensor. Suitable sensors for use in this context are known to those of ordinary skill in the art. See for example the sensor described in U.S. Pat. No. 3,421,362 and entitled DEVICE OR APPARATUS FOR DETECTING IN AIR THE PRESENCE OF COMBUSTIBLE OR INFLAMMABLE GASES. Other types of sensors are also suitable for this use and therefore detailed understanding of the sensor elements itself is not necessary to understanding the entire invention. The active sensor element 81 is preferably connected across terminals 78 and 79. The reference sensor element 83 is preferably connected across terminals 80 and 82.

The purpose of having two sensors elements 81 and 83 is to have both elements respond to variations in ambient conditions such as temperature and humidity but have only one sensor element respond to the presence of hazardous gases. Therefore both sensors are identical but the active sensor element 81 is only responsive to gas since the reference sensor element 83 is desensitized with a thin coating of glass or lead.

The analog signal from reference sensor element 83 passes through a zero adjust potentiometer 84 "P1" and forms one input to differential amplifier 86. The other input to differential amplifier 86 comes from the active sensor element 81. The analog output from differential amplifier 86 forms one input to differential amplifier 88. The analog output from differential amplifier 86 is in direct proportion to the difference between the analog signals received from reference sensor element 83 and active sensor element 81. Zero adjust potentiometer 84 does not have to be adjusted frequently. It acts as a coarse adjustment and helps to improve the overall accuracy of the instrument. Resistors R46 element 87 and R47 element 89 act as a voltage divider to provide a reference signal to the other input of differential amplifier 88. Therefore, the output of differential amplifier 88 is an analog signal proportional to the difference between the signals from sensors 81 and 83 and the reference potential as established by the voltage divider signal applied at the other input to differential amplifier 88. The analog output from amplifier 88 passes through resistor 91 (R21—18K ohms) and through pin 35 "INHI" back to A/D converter 52. The analog output of amplifier 88 may also be directly measured at the analog output terminal 108 for field test purposes.

The digital output and interfacing control lines of analog to digital converter 52 appear at terminals "CE/Load"; "Send", B-1 through B-12 and "POL". Those terminals are respectively and selectively connected to pins 22, 23 and 26 through 33 of UART 50. Also identified as pins TBRL; TBRE, TBR1 through TBR8. Once the mode pin of the A/D converter 52 automatically transfers the upper and lower bytes to UART 50 A/D converter 52 feeds its digital information to UART 50 in two bytes S1 through S8 and S12 through S19 as previously described and as illustrated in FIG. 3E. A/D terminals DRR, TBR6, TBR7 and TBR8 are fed from the tri-state hex buffer 62. The A/D converter 52 puts out the upper byte which consists of the signals on terminals B9, B10, B11 and B12 and polarity. That leaves three places in the upper byte where additional information can be added into the transmit train (bits S6, S7 and S8). The three information places not used by the A/D converter upper byte go to UART pins 31, 32 and 33. They are attached to the tri-state hex buffer 62 and when that is enabled it will put out information into the transmit buffer consisting of one signal that is an error signal at pin 6 of the tri-state buffer 62 and two signals that are connected to push buttons used for a calibration request at pins 2 and 4 of tri-state hex buffer 62. Those outputs appear as terminals 104 and 106 from the tri-state hex buffer 62 and are attached to push buttons which will initiate a "span" request or "zero" request respectively. Once the upper byte has been transferred to the UART the A/D converter 52 puts out the lower byte.

Tri-state hex buffer 62 is used to add in three bits to the upper byte as it is transferred in parallel to UART 50. That information is changed from parallel to serial form and transmitted through UART terminal TR0 and LED/phototransistor set 48 and ultimately appears across terminals 110 and 112 for transmission back to CPU satellite sub-assembly 12. It is important to note that the responding byte from each sensor 15 has a parity bit that is automatically opposite to the parity bit received from the CPU satellite sub-assembly 12. In the present examples shown in FIG. 3E the CPU transmits with an odd parity bit at bit location C9 and the sensor 15 responds with even parity bits at bit locations S9 and S20.

Power for the sensor appears across terminals 78 and 100 and may come from any direct current source in the range of 10 to 32 volts. A positive 5 volt regulator 96 provides +5 volt power to all integrated circuits including UART 50 and A/D converter 52. Circuit 98 converts the positive 5 volts DC to negative 5 volts DC and acts as the negative power supply for the integrated circuits. The +10-32 volt DC input terminal 100 is also connected to a constant current source 94 which typically puts out 500 milliamperes for heating sensor elements 81 and 83. The output of constant current source 94 is also connected to continuity detector 90 whose output is connected across the sensors 81 and 83 and also as an input to tri-state hex buffer 62 and to A/D converter 52. Continuity detector 90 automatically determines if there is an internal error in the electrical system and, if an error exists, produces an input to the tri-state hex buffer 62 so that the error data is transmitted back to the satellite subassembly 12 where an operator can take corrective action. As shown in FIGS. 3A-3D, a portion of the input voltage (preferably 24 volts DC) is connected to terminal 102 and provides the power to drive the solenoids 38 and 42 which are controlled by the signals across terminals 74 and 76. Continuity detector 90 is fed by a voltage regulating amplifier 92 which forms one input. The other input comes from a voltage divider attached to the output of constant current source 94. The "sensor current" can be measured directly across the input pin to the continuity detector circuit 90. As previously described, the output from continuity detector 90 forms one input at pin 6 to the tristate hex buffer 62. "Continuity" is in a "wired-or" configuration with "overrange (or)" of the A/D. Each is an independent error signal but they are combined to form a single error bit.

Figure 4B:
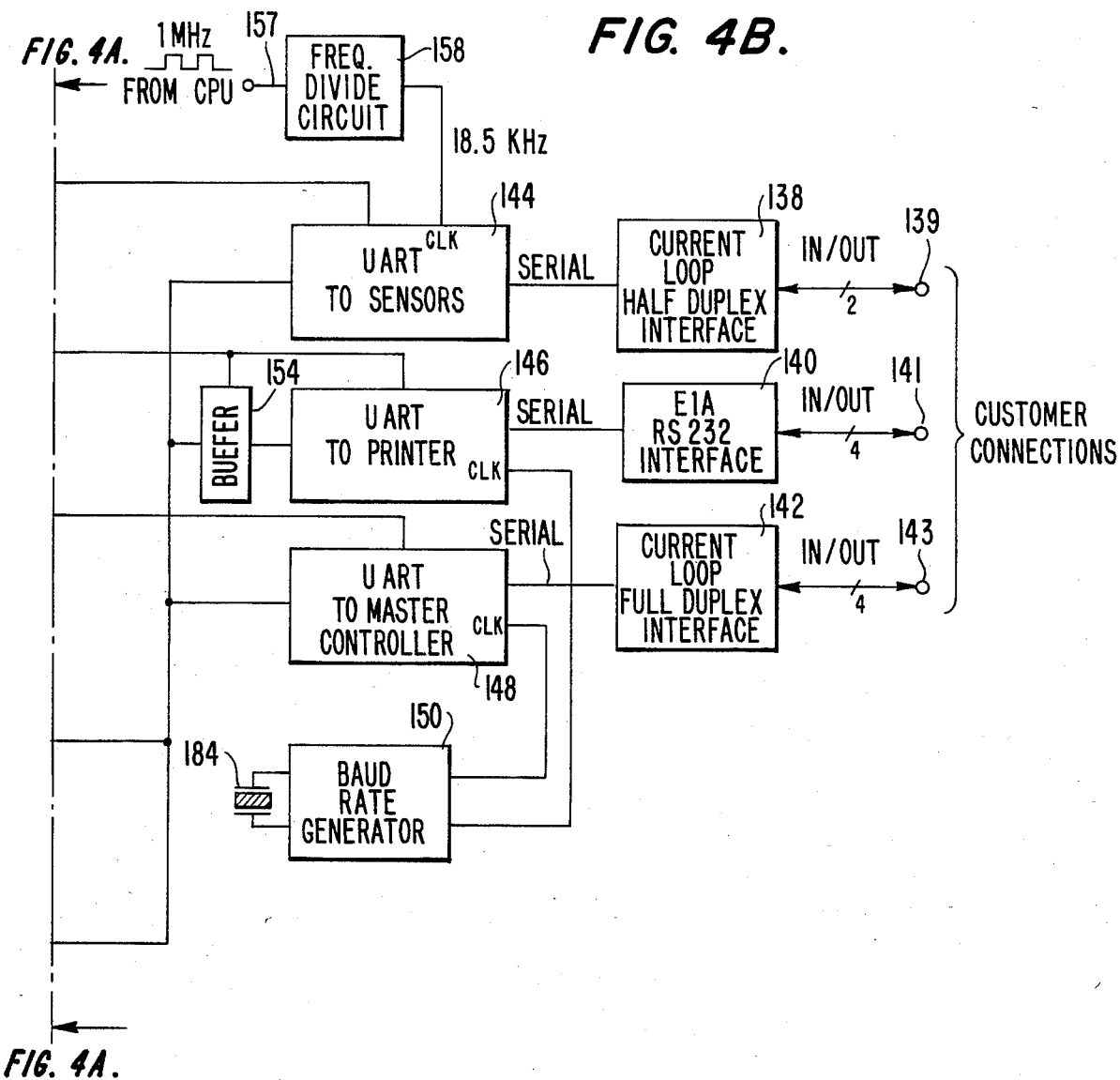

The function of the satellite subassembly 15 can be understood by referring to FIGS. 4A and 4B. The heart of the CPU section 26 is the 8 bit Microprocessor 120. Microprocessor 120 takes its intruction from PROM 126 as fed through the Address Decoding and Control Logic circuit 122. Microprocessor 120 also receives other information from address decoding and control logic circuit 122 and operates on the information stored in RAM storage memory 124. PROM 126 may be an EPROM (Erasable Programmable Read Only Memory) which is non-volatile, meaning that if power is lost to the system the CPU 26 goes to the PROM 126 memory first in an organized way and starts itself up again. Battery Back Up and Recharge Circuit 128 supplies continuous power to RAM storage memory 124. Battery circuit 128 is supplied with a constant current input at terminal 178 and with plus 5 volts DC at terminal 180. An AC power failure detection circuit 130 provides a power fail signal $\overline{PWRF}$ to Microprocessor 120 and is supplied with 8 volts AC/60 cycle signal from a conventional power source supplied to terminal 176.

Outputs from the CPU section 26 ultimately go to channel relays 32, customer connections 31, the front panel display 30 and the printer unit 34. A latch circuit 132 is provided between the CPU section 26 and the channel relays 32. Similarly a latch circuit 136 is located between the connections to the front panel 30 and CPU section 26. A set of master relays 28 is located between the customer connections 31 and a latch circuit 134 connected to the output of CPU section 26. A return circuit 29 from the front panel 30 forms another input to latch circuits 132, 134 and 136.

Outputs from CPU section 26 also pass through UARTS 144, 146 and 148. An 18.5K Hertz clock input to UART sensor 144 comes from frequency divider circuit 158 which receives a 1 mega Hertz input on terminal 157. The output of UART 144 passes through Current Loop Path Duplex Interface circuit 138 and appears on terminal 139. Printer UART 146 receives one input from the Address Decoding and Control Logic circuit 122 and another input through buffer 154 from Microprocessor 120. The serial output from Printer UART 146 passes through an RS 232 Interface 140 to input/output terminal 141. The output of the Master Controller UART 148 passes through Curret Loop Full Duplex Interface 142 to input/output terminal 143. A Baud Rate Generator 150 controlled by a crystal frequency standard 184 provides a clock input to Printer UART 146 and the Master Controller UART 148.

Figure 4C:
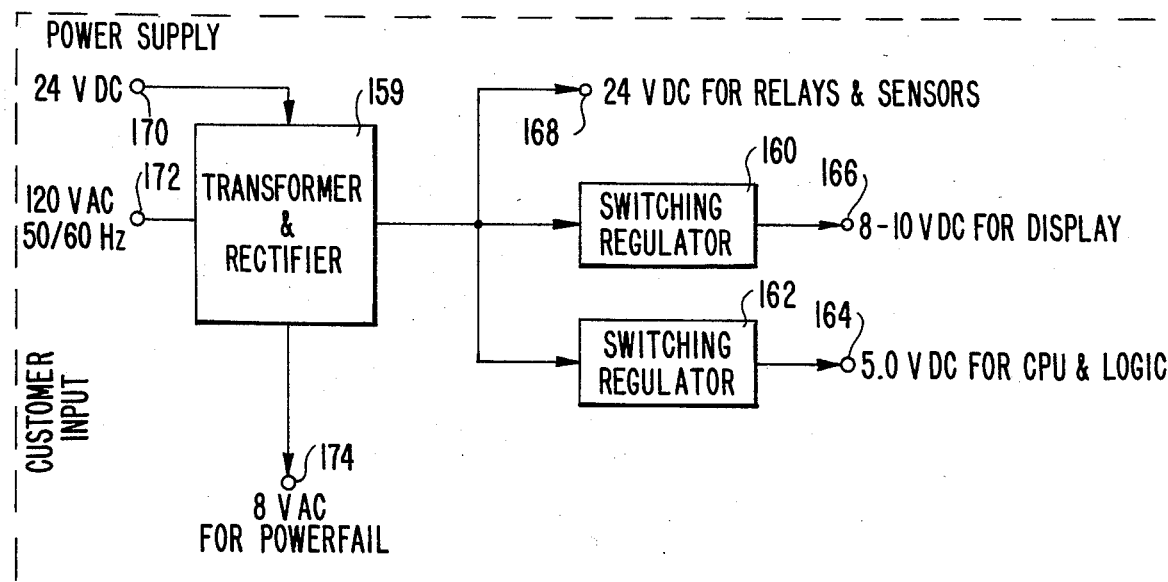
FIG. 4C is a functional block diagram of the power supply for the satellite subassembly unit illustrated in FIGS. 4A-4B.

The power supply circuitry for the satellite unit of FIG. 4A is illustrated in FIG. 4C. A Transformer and a Rectifier circuit 159 receives 24 volts on terminal 170, 120 volts AC 50/60 cycles on terminal 172 and supplies 8 volts AC on terminal 174 for detection of power failure. Transformer and Rectifier Circuit 159 produces 24 volts DC at terminal 168 for powering the relays and sensors of the system. A switching regulator 160 converts 24 volts DC to 8-10 volts DC at terminal 166 for driving the display circuitry. Switching Regulator 162 provides 5.0 volts DC at terminal 164 for the CPU and Control Logic circuit 122.

Figure 5A:
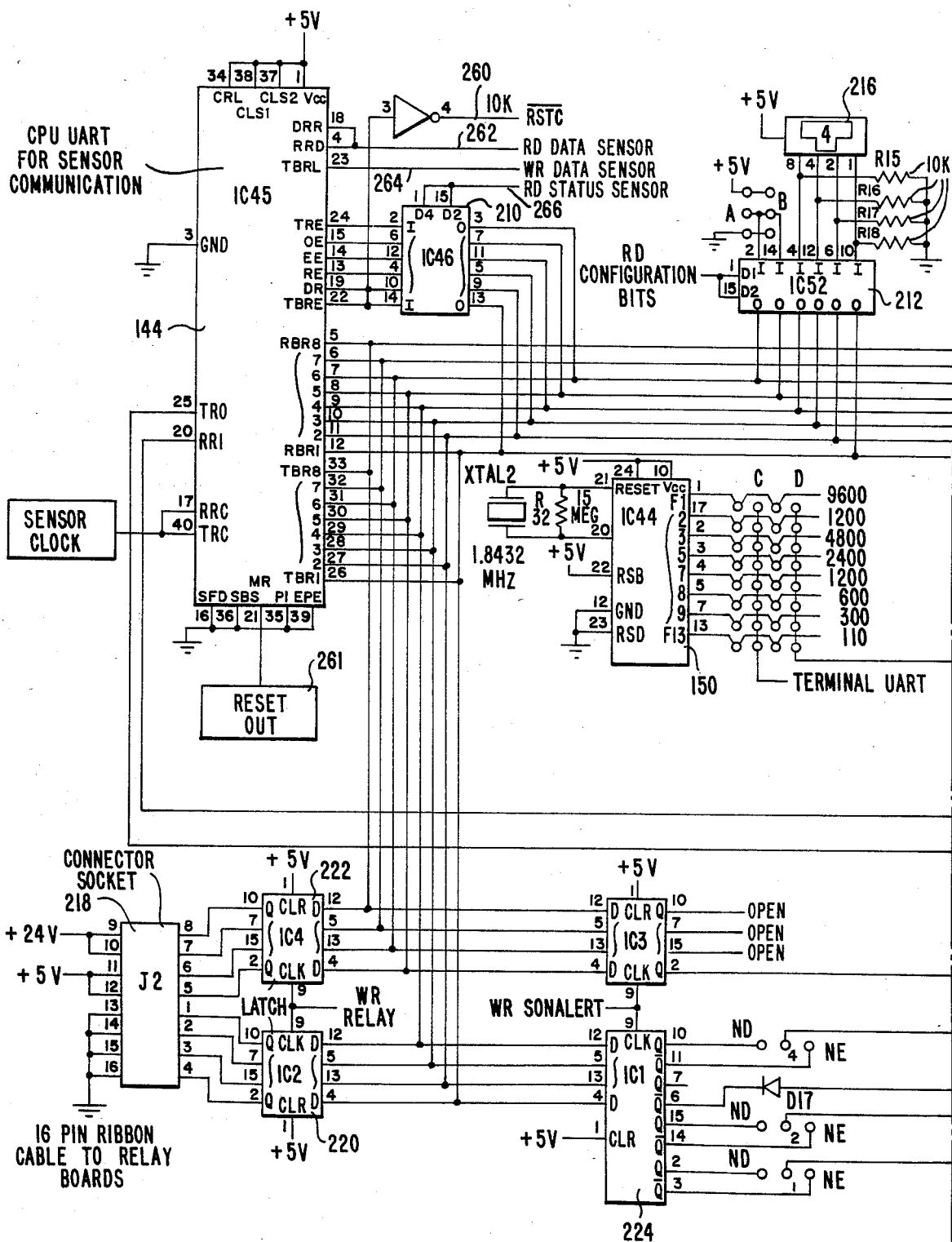
FIGS. 5A-5B illustrates the communications and relay control logic for the CPU unit of FIGS. 4A-4B.
Figure 5B:
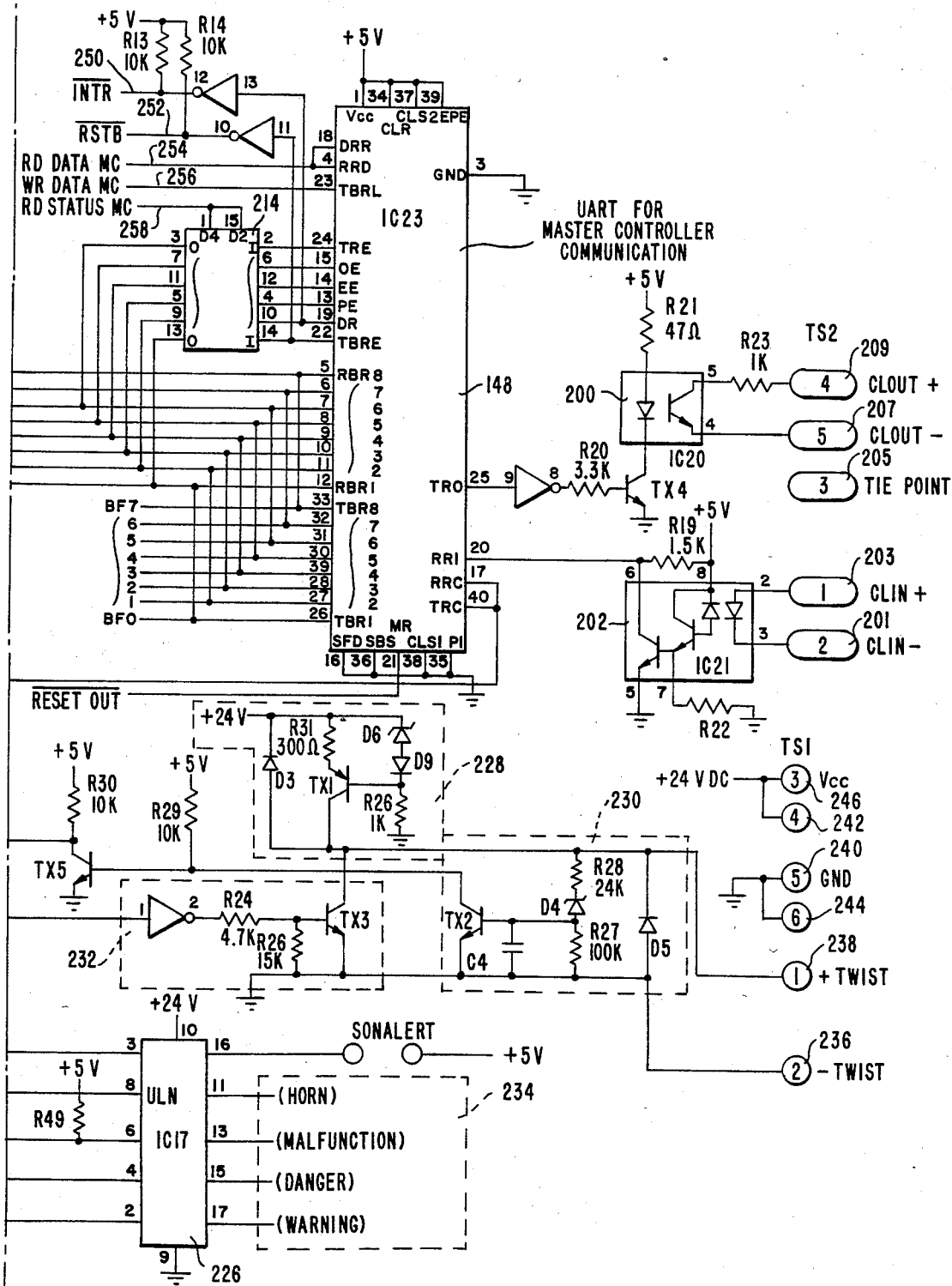

Details of the circuitry illustrated in FIGS. 4A-4B are shown in sub diagrams 5A through 5I. FIGS. 5A-5B illustrates the details of the communications and relay control logic for the CPU 26 board. The Master Controller UART 148 is connected through an LED/phototransistor isolator 200 to output terminals 207 and 209. Terminal 205 serves as a tie point. An input for the Master Controller UART 148 goes through the LED phototransistor isolator 202 from terminals 201 and 203. Terminals 242 and 246 are connected to a service of 24 volts DC such as terminal 168 illustrated in FIG. 4C. Terminals 240 and 244 are both connected to ground. Terminals 236 and 238 serve as communication lines to the sensors. CPU Sensor UART 144 transmits via two terminals 236 and 238 through output contacts TR0 and RRI. The elements noted as 232 form part of the CPU transmission circuitry whereas the elements designated as 230 act as part of the CPU receiving and amplifying circuitry. Current Source 228 provides power to the CPU transmit circuit 232 and the CPU receiving circuit 230.

Selection switch 216 and tri-state buffer 212 comprise the address selection circuitry for CPU26. CPU 26 may refer to its own address for use in communicating with master controller 24 by signalling buffer 212 via address decoding and control logic 122.

Tri-state input and output terminals TBR1-TRB8 and RBR1-RBR8 of UARTS 144 and 148 are connected to microprocessor 120 input/output terminals AD0-AD7. Address decoding and control logic 122 interprets microprocessor 120 signals and controls the transfer of information between microprocessor 120 and UARTS 144 and 148. Latch circuits 220 and 222 are likewise connected to microprocessor 120 input/output terminals AD0-AD7. Address decoding and control logic 122 interprets microprocessor 120 signals and controls the latching of data by circuits 220 and 222. Data thus latched is transferred to socket connector 218 which accomodates a 16 pin ribbon cable connector for channel relay assembly 22. Master relays 29 are driven by relay connections 234 which are the outputs of circuit 226. Circuit 226 inputs are attached to latch 224 which receives signals from microprocessor 120. Relay connections 234 consist of a horn, a malfunctions signal, a danger signal, and a warning signal. The malfunction signal depends upon the output of IC18 monostable which is regularly serviced by microprocessor 120. Should the microprocessor 120 either detect a system malfunction or fail to service IC18, IC18's output will fall and the master malfunction relay will de-energize. Thus the system is protected from malfunctions detected and also total system failure such as "CPU stopped". Other important output terminals from circuit in FIGS. 5A-5B include $\overline{\text{INTR}}$ terminal 250, $\overline{\text{RSTB}}$ 252, RD Data MC terminal 254, WR Data MC Terminal 256 and RD Status MC 258. The foregoing are all associated with the Master Controller UART 148. The following terminals are associated with the CPU UART 144: $\overline{\text{RSTC}}$ terminal 260, RD Data Sensor Terminal 262, WR Data Sensor Terminal 264 and RD Data Status Sensor 266. A Reset Out Terminal 261 is connected to contact MR on the CPU UART 144.

Figure 5C:
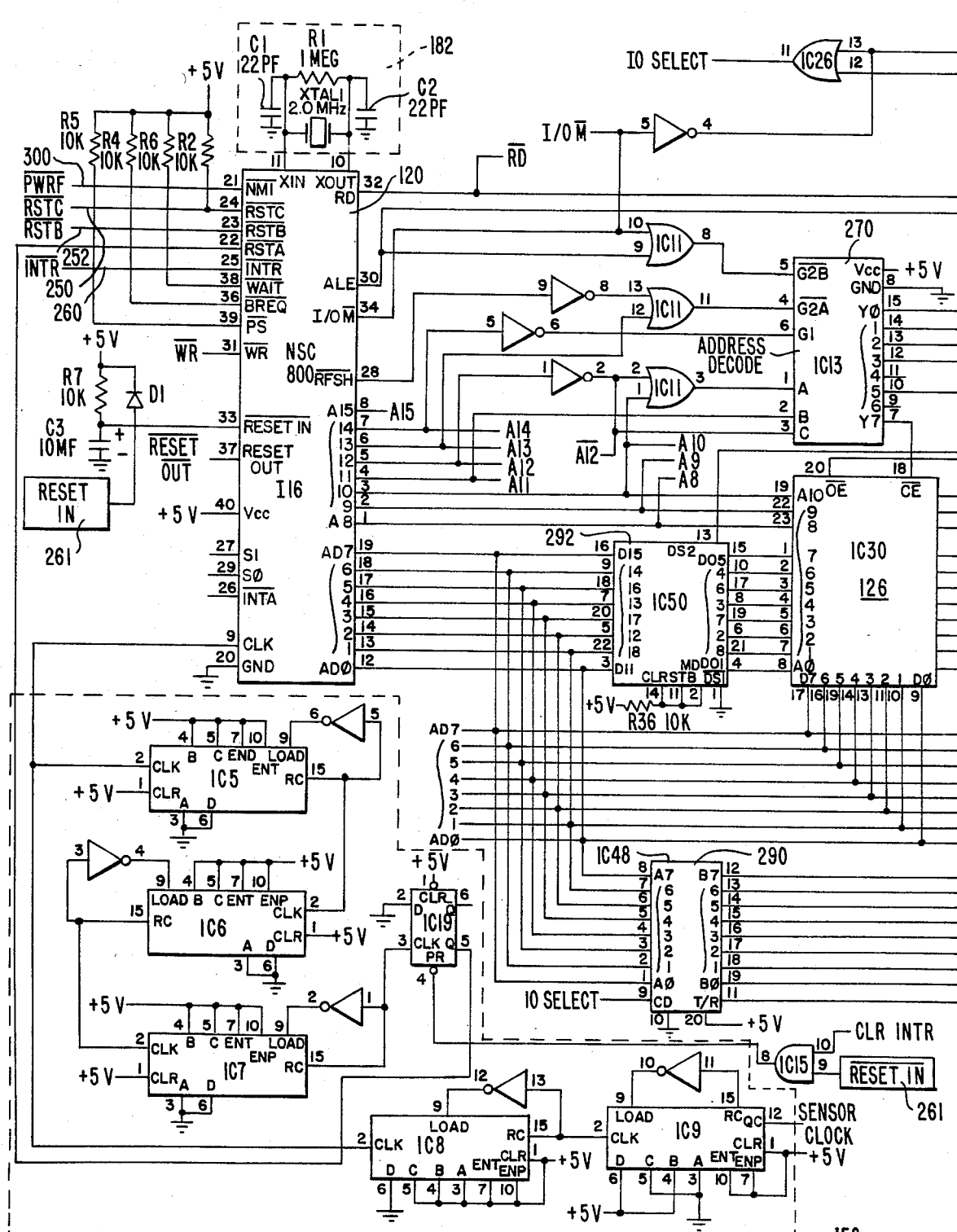
FIGS. 5C-5D illustrate further details of the CPU and the control logic as found on the CPU unit of FIGS. 4A-4B.
Figure 5D:
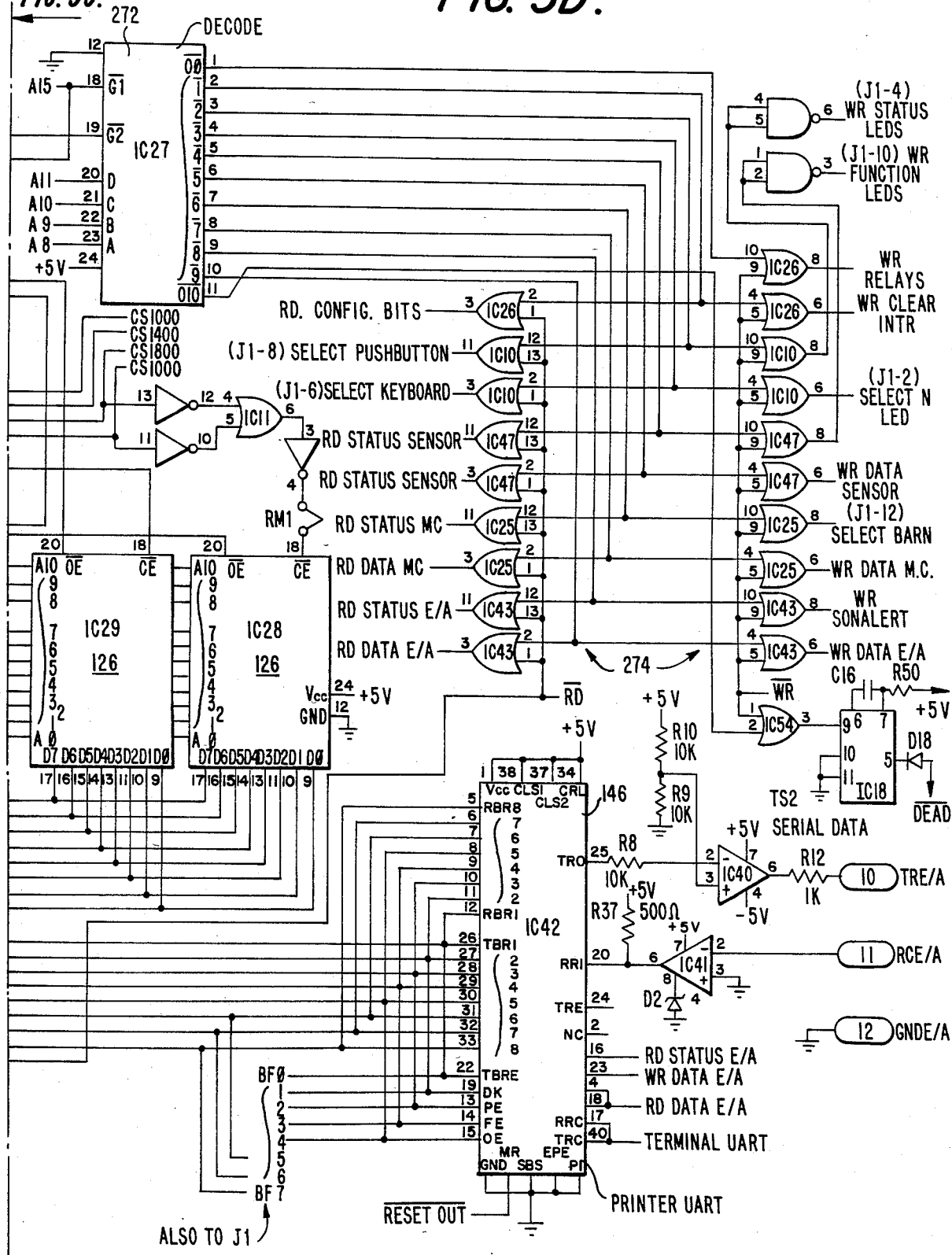

FIGS. 5C-5D illustrate the Microprocessor and control logic for the CPU board. Microprocessor 120 is connected to a 2.0 mega hertz frequency standard 182 which serves as a clock input. Microprocessor 120 receives input from three PROM sections 126 through bus transceiver 292 at terminals AD0 through AD7. The same contacts are connected through bus transceiver 290 to input terminals TBR1 through TBR8 of printer UART 146. Other inputs to microprocessor 120 comprises $\overline{\text{INTR}}$ 250, $\overline{\text{RSTB}}$ 252, $\overline{\text{RSTC}}$ 260 and $\overline{\text{PWRF}}$ 300. CLK is an output which goes to freq divide circuitry to generatre both the sensor UART clock and a 1 ms interrupt RSTA for a real time software clock. Outputs from microprocessor 120 also go to the Address Decode Circuit 270 for control of the PROM circuits 126. Other leads go to Decode Circuit 272 which in turn go to a plurality of NAND gates 274 which provide the control signals for a variety of different circuit functions.

Figure 5E:
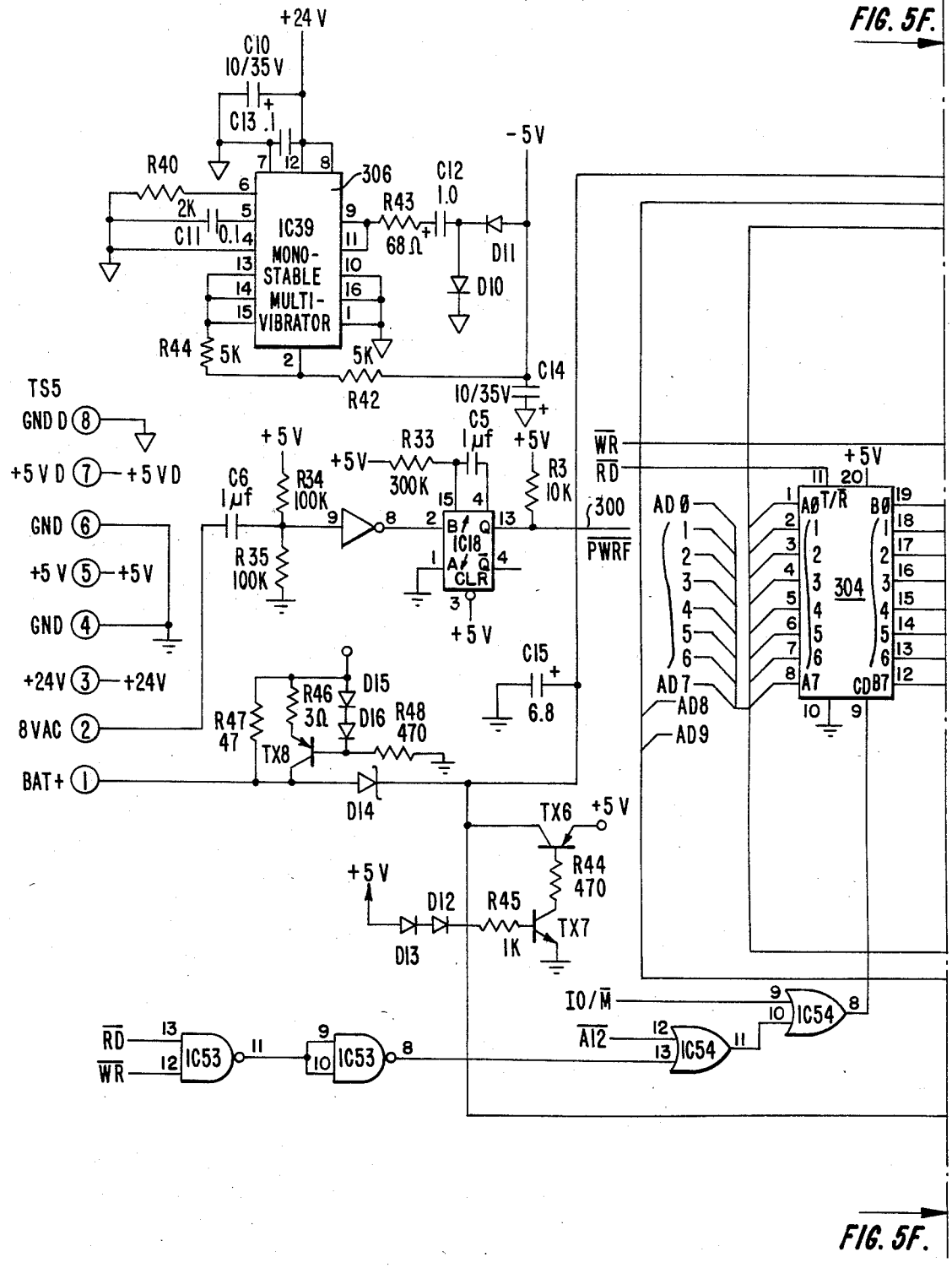
FIGS. 5E-5F illustrate the RAM memory and battery back up for the CPU unit of FIGS. 4A-4B.
Figure 5F:
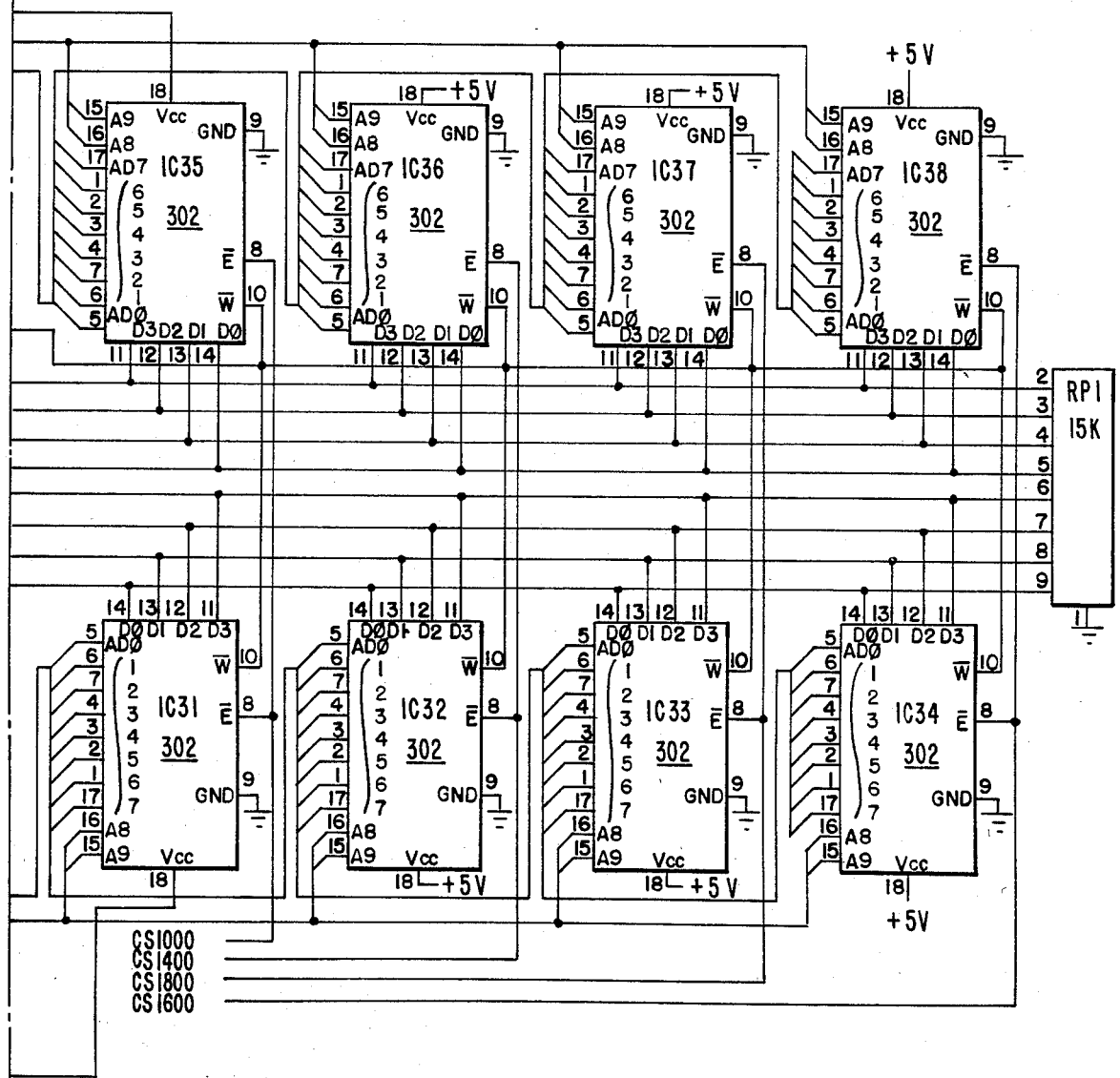

FIGS. 5E-5F illustrate the RAM memory and battery back up circuitry for the CPU board. Eight RAM chips 302 comprise the active RAM memory of the circuit. Every RAM circuit 302 contains one thousand 4 bit portions. Each RAM circuit 302 is arranged in pairs across the data lines with another RAM circuit 302 in order to create an 8 bit byte. Integrated circuit 304 forms an interface with the other portions of the CPU 26.

A one shot, Monostabile Multivibrator 306 is triggered by the 60 Hertz signal from the AC power line. If any of the 60 cycle pulses are missing the one shot output will fall because it needs the 60 cycle pulses every few milliseconds to keep its output high. If the 60 Hertz signal fails then the output of Monostabile Multivibrator 306 goes low and it puts a interrupt signal on the power failure terminal 300 $\overline{\text{PWRF}}$. Between the time that the monostabile 306 detects a power failure and the power actually goes dead, the CPU 26 stops everything, adds up all of the contents of the RAM memory 302 into a data number and stores that number in the RAM while it waits for the power to come on. The RAM is kept alive by the rechargable battery circuit that comprises part of the system. The DC power to the RAM can keep the memory alive for a long time. When the power goes back on the CPU interrogates the RAM 302 memory, adds up all the memory contents again, and retrieves the number that it put away prior to its loss of power and compares that number with the contents of the RAM 302 to determine if any RAM memory has been lost. If the two numbers are different the circuit will go through a "cold start" procedure which would include recalibration of variables, etc. However, if the current RAM memory is the same as the number stored prior to power failure, then the circuit will resume on a "warm start" basis which does not require recalibration. Basically the three circuits described in FIGS. 5A-5F comprise the CPU unit 26.

Figure 5G:
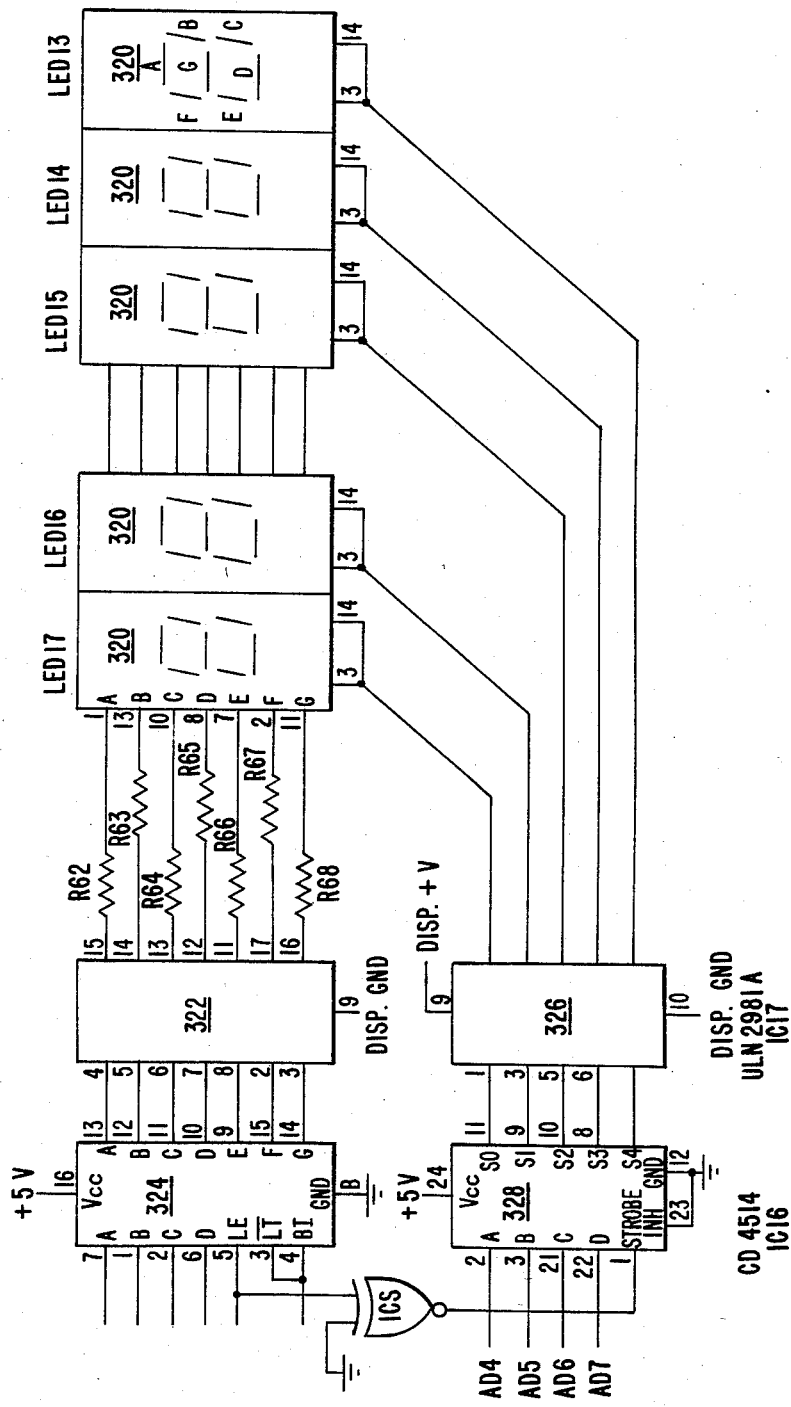
FIG. 5G illustrates the control display logic of the CPU unit of FIGS. 4A-4B.

The output of the display panel is produced on LED elements 320 as illustrated in FIG. 5G. Circuit elements 322 and 324 provide the drive for certain segments of the LED display 320. A 4-to-16 decoder with latch circuit 328 drives a Quad Exclusive NOR gate 326 which provides the other input to LED display 320.

Figure 5H:
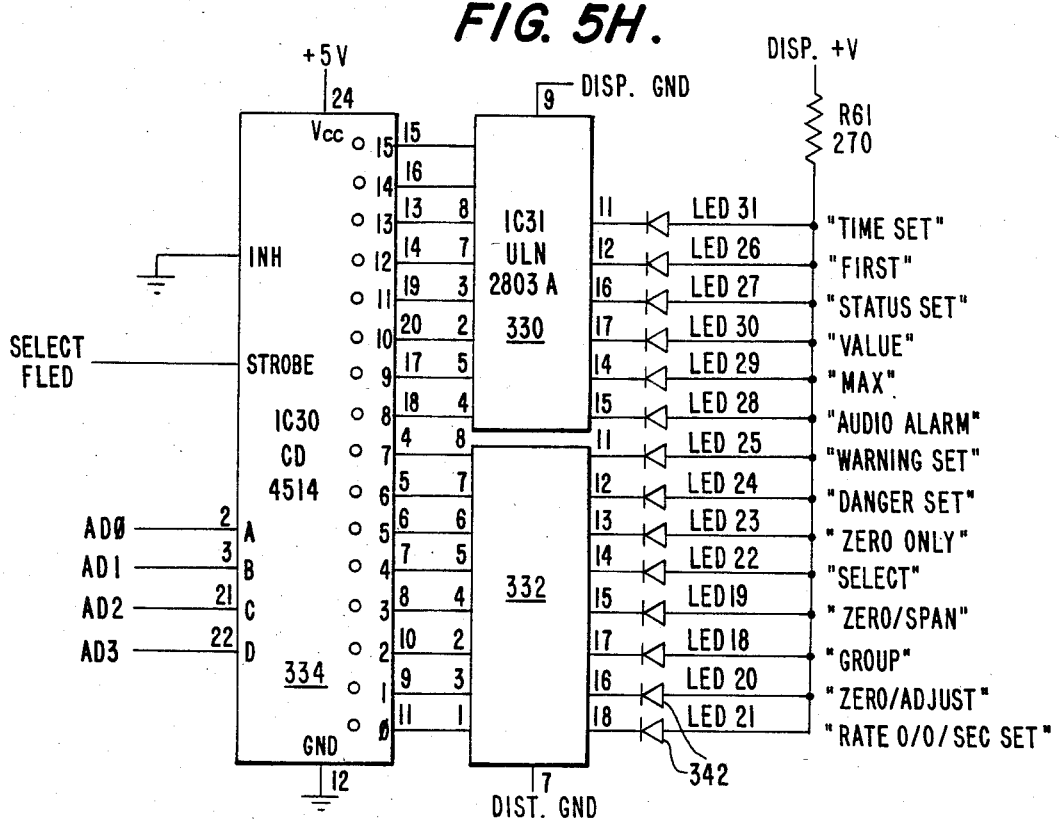
FIG. 5H illustrates the control LED "Warning light" logic for the CPU unit of FIGS. 4A-4B.

FIG. 5H illustrates further control LED logic. A Decoder with Latch circuit 334 feeds two logic gates 330 and 332 to produce the logic output signals illustrated at the output of the gate. LED's 342 shown as LED 18 through LED 31 provide warning lights indicating that a signal is present. The display circuitry described in FIG. 5G provides a numeric output giving specific values. Whereas the purpose of the circuitry in FIG. 5H is to provide "idiot light" or "warning light" indications of the status of the equipment. For example, the circuitry in FIG. 5G might indicate the actual gas concentration measured by the sensors 15.

Figure 5I:
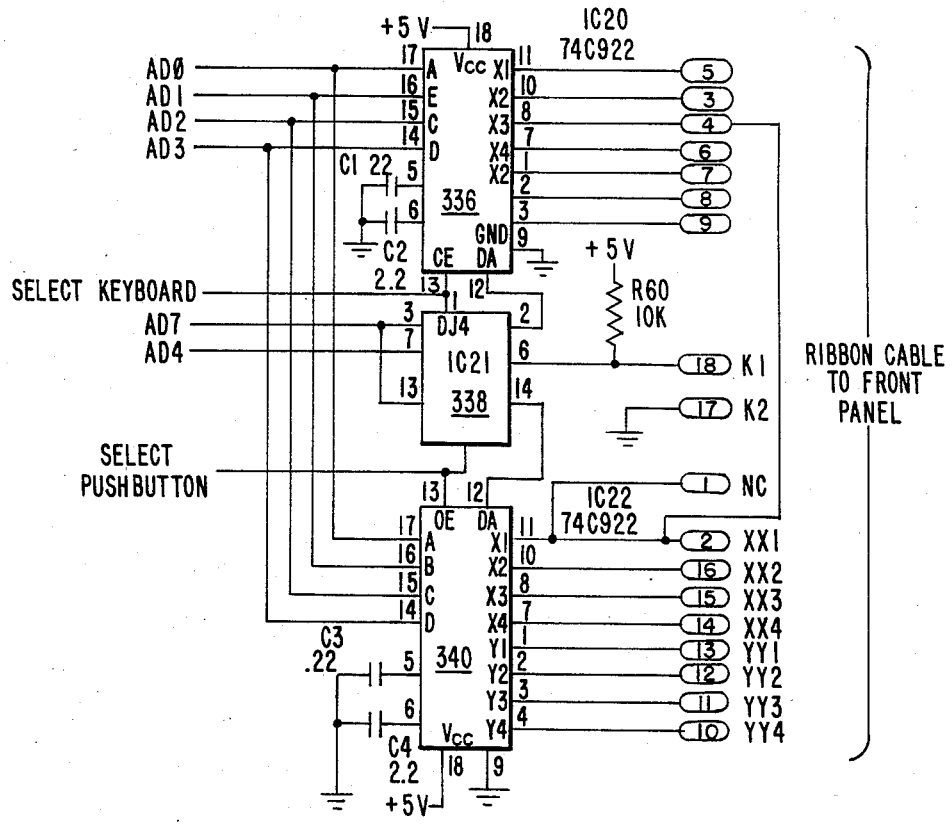
FIG. 5I illustrates the panel switch logic of the CPU unit of FIGS. 4A-4B.

Lastly, FIG. 5I describes the panel switch logic. "Select keyboard" and "Select push button" signals are provided to integrated circuits 336, 338 and 340. Decoded outputs provide specific instructions to other parts of the CPU 26 in response to the input from the keyboard.

The following is a parts list of the major elements which comprise portions of the circuitry just described. All of the major elements of the apparatus are conventional and may be purchased from electronic dealers as 1. CPU (Element 120) National NSC 800N-1
2. UART (Elements 144, 146, 148) Intersil IM6402IP
3. Optoisolator Line Receiver (Elements 46, 202) Hewett Packard 6N139
4. Optoisolator, Darlington Transistor (Elements 48,200) TIL119
5. Quad Operational Amplifier (Elements 86, 88, 90,92) RCA CA324G
6. A/D Converter (Element 52) Intersil ICL7109CPL
7. CMOS Binary Counter (Element 158 in part) National MM74C161
8. CMOS Quad D Flip-Flop (Elements 64, 220, 222, 224) National MM74C175
9. CMOS Tristate Hex Buff (Element 62) National MM80C97

10. CMOS 3 Input NAND (Elements 58, 60) National MM784C10
11. CMOS 4 Bit Comparator (Element 54) National MM 74C85
12. Negative Voltage Supply (Element 98) Intersil ICL7660
13. CMOS Dual D Flip Flop (Element 158 in part) National MM74C74
14. CMOS 4 to 16 Decoder (Element 122 in part) National MM74C154
14. CMOS Quad 2 Input or Gate (Element 274, 122 in part) National MM74PC32
16. CMOS 3 to 8 Decoder (Element 122 in part) National MM74PC138
17. Hex Inverting TTL Buffer (Element 122 in part) National MM74C901
18. CMOS 8 Bit Bidirectional Transceiver (Element 304) National MM82PC-08
19. CMOS 4 to 16 Decoder w/Latch (Element 328) National CD4514
20. CMOS Quad Exclusive NOR Gate (Element 326) RCW CD40778E
21. CMOS Key Endoer (Elements 336, 340) National MM74C922
22. CMOS BCD to 7 Seq. Decoder (Element 324) National MM74C48
23. CMOS Hex Inverter (Element 122 in part) National MM74PC04
24. General Purpose Voltage Regulator (Element 94) Fairchild UA723PC
25. CMOS 8 Bit I/O Port (Element 292) National MM82PC12
26. CMOS Quad 2 Input and Gate (Element 122 in part) National MM74C08
27. CMOS Schmidt Trigger (Element 158 in part) National MM74C14
28. Quad 2 Input NAND TTLLP (Element 122 in part) 74LS00
29. Dual Monostable TTLLP (Element 306) 74LS123
30. Baud Rate Generator (Element 150) Motorola MC14411
31. CMOS EPROM (Element 126) National NM 27C16
32. CMOS Static RAM (Element 302) National NMC6514J-S
33. Crystal 2.000 MHZ (Element 182) CTS MPO-20
34. Crystal 1.8432 MHZ (Element 184) CTS MPO-181
35. Address Switch (Element 56) EECO 24 0004G or Equivalent
36. 8 Place Darlington Array (Element 226) Sprague ULN 2803
37. Rotary Address Switch (Element 216) Interswitch GWS 306180
38. 5 Volt Positive Regulator (Element 96) Fairchild VA78M05HC
39. 1 AMP Relay DPDT (Element 28) Sigma 60RE2-24V In summary, the operation of the system is as follows. The master controller circuit 24 can signal a request for calibration or information concerning any sensor 15 attached to satellite 12. The CPU section 26 generates an 8 bit digital transmission C1–C8 which includes an odd parity bit in the C9 location. The first four bits C1–C4 are the address portion of the transmission. If the address transmitted by the satellite system 12 corresponds to the address selected by circuit 56 of an individual sensor assembly 14, then the sensor assembly 14 will respond with two 8 bit digital words having an even parity bit at the end of each 8 bit word response. The satellite subassembly 12 will recognize the two bytes as a correct response from a sensor 15 and will record the information it is RAM memory 302. In addition the other non-addressed sensors 15 will recognize that the transmission from the addressed sensor 15 is not its own since the information from the addressed sensor 15 has an even parity. In this manner the sensors 15 can discriminate between transmission from other sensors (which have even parity bits) and transmission from the satellite subassembly 12 (which has odd parity bits).

The apparatus 10 calibrates itself internally in the following manner. A calibration request is received by the satellite assembly 12 from either the master controller 24 or the remote sensor assembly 14 of the display assembly 30. Subassembly 12 will provide a digital dignal at the C7 bit location requesting that the Zero Gas Solenoid 38 turn on. The turn on period can be varied but would typically be in the range of thirty seconds. The sensor unit 15 will take the reading, convert the result from analog to digital and transmit it back to the satellite subassembly 12 as part of its two byte digital response includings bits 50 through 521. The CPU 26 will store that information for later use. The satellite subassembly 12 then calls for activation of the span gas by means of a data bit at the C8 location. The sensor 15 responds by trning on solenoid 42 for a period of time allowing the span gas 44 to be measured by the sensor elements 81 and 83 in the same fashion that the zero gas 40 was previously measured. The master controller 24 can determine how long the span gas is applied to the sensors. As previously described the zero gas is preferably uncontaminated air at 3 lbs. per square inch and the span as is preferably a 2% mixture of hydrogen with 98% uncontaminated air at 3 lbs. per square inch. The reading of the span gas 44 is converted from analog to digita and transmitted back to the Satellite Subassembly 12 where it is stored by the CPU 26. An internal program in the Satellite Subassembly 12 takes the readings from the zero gas and span gas and extrapolates them to a linear curve. All subsequent readings from the sensor units 15 are compared to their individual zero gas/span gas curves and the resulting interpolation gives a very accurate reading of the actual gas present where the sensor unit 15 is located.

The gas detection system just described has several advantages over the prior art. One major advantage is in the cost of installation. Many prior art systems require multiple wiring to sensors. The present invention only requires two wires to be attached to each sensor and each sensor can be connected in parallel to the previous sensor. This approach can cut the cost of wiring down to one third of that associated with many other prior art systems. It has been found that the installation costs of prior art systems can be twice as much as the cost of the instruments that comprises the systems. This particular system is especially adapted for the detection of hazardous gases in refinerys. Prior art gas detection systems required special types of explosion proof piping to protect wiring. Many of the sensors are frequently several thousand feet away from the main controller and, when the cost of wiring an be as high as $2.00 per foot, the ultimate cost of the gas detection system can be extremely high. Note also that the presence of information at the sensor assembly 14, especially the alarm indicator and alarm relay, may eliminate the need for additional wiring of alarms, horns, sirens, fans or dampers from the satellite assembly 12 to the remote sensor 15 location which may be several thousand feet removed from the satellite assembly 12. Typically, information indicators or alarms are not available at the sensor location. Therefore, the present invention is relatively inexpensive to install becaue only two wires are required for all the sensors. It is possible to employ only two wires for all the sensors because of the unique digital sending and receiving system employed. In particular, Applicant's unique use for the parity bit information provides the following two advantages:

a. It allows for the detection of errors in the transmission or reception signals.

b. It allows the CPU unit 26 to identify a transmission from a particular sensor 15 while the other sensors ignore the response of the particular sensor 15 addressed by the CPU 26.

Another major advantage of the invention is that it readily allows the system operator to calibrate the equipment from a remote location. Only one operator is necessary. It is not necessary to have an operator at the actual location of a sensor 15 unless the sensor mechanism itself is broken. Therefore, the present invention represents a true one operator system. The system therefore not only saves costs in terms of salaries and operating expenses, but also is much safer in that it does not require a maintenance person to enter a hazardous gas area in order to perform routine recalibration of the sensors.

The "time out" feature of the invention may be somewhat unique. If the satellite subassembly 12 does not get a response back from a particular sensor within a predetermined period of time then it knows it has a sensor malfunction and so indicates to the system operator. Similarly, if there is a power failure the Monostable Multivibrator 306 will cause the CPU to store a single data sum in RAM until power is restored. If the prefailure data sum is the same as the post failure sum then the device can resume performing on a "warm start up" basis. If not, a lengthy "cold start up" is required. Also it is possible for the device to calibrate sensors simultaneously in groups or they can be tested individually one at a time. If further economics are desired it is further possible to cut down on the number of gas solenoids required by "ganging" groups of sensors 15 together and feeding them through common "Zero" and "Span" solenoids 38 and 42.

The invention has the additional advantage that it does not require a common ground potential and a remote power supply can be used thereby eliminating the need for long power wire runs. This advantage is obtained because of the optoisolation built into the system and the use of remote power regulation. Furthermore, since the sensors can receive information no additional wiring is needed for an alarm, a relay or indicators at the remote sensor locations.

There are several modifications that could be made to the present invention. For example, it would be readily possible to employ fiberoptics to connect each satellite of subassembly 12 to the associated sensor units 15. Fiberoptic connections might be a little bit more expensive, however, they have the advantage of being non-conductive and therefore immune to causing sparks and accidental explosions in hazardous gas atmosphere. Also, other types of integrated circuits available from other manufacturers might be employed as well. For example, the size of the RAM memory could be increased or a different type of microprocessor could be used if more than 16 sensors were employed per satellite subassembly 12.

While the invention has been described with reference to the preferred embodiment thereof, it will be appreciated by those of ordinary skill in the art that modifications can be made to the components and methods of the invention without departing from the spirit and scope thereof.

We claim:

1. A gas sensing system comprising:
   a satellite means including a central processing unit (CPU) means for controlling said system and for transmitting information in a digital code having a predetermined number of bits;
   a single pair of information leads;
   sensor means attached to said satellite means by said single pair of information leads;
   a source of zero calibration gas;
   a source of span gas;
   valve means for applying said zero calibration gas and said span gas to said sensor means;
   a master controller means for controlling a plurality of satellite means;
   a parity determining means within said sensor means for generating a digital word in response to interrogation from said satellite means which differs by one parity bit from the digital word generated by said satellite means so that said satellite means can recognize that it is getting a response from the addressed sensor means and so that the non-addressed sensor means recognizes that the digital word is not coming from said satellite means;
   a sensor universal receiver/transmitter means (UART) for sending and receiving signals to and from said satellite means and for generating a parity error bit signal and a data ready bit signal;
   an address selection means for generating a digital address for a given sensor means different from the digital address of other sensor means associated with a given satellite means;
   comparator means for comparing the address of an incoming digital signal with the address selected by the address selection means and for producing an output if the address of the incoming digital signal is the same as the address selected by the address selection means; and,
   gate means for producing an output in response to an input from said comparator means and the presence of a parity error bit signal and a data ready bit signal from said sensor UART,
   wherein said satellite means communicates to said sensor means and said sensor means communicates with said satellite means exclusively on said single pair of information leads and wherein the application of said zero calibration gas sets a zero point for said sensor means and application of said span gas sets an intermediate range point for said sensor means whereby said CPU takes both said zero point and said intermediate range point and extrapolates the actual value of subsequent gas measurements from said two points.

2. The system of claim 1 wherein said sensor means further comprises:
   sensor elements whose electrical characteristics respond to gas in the environment;
   analog to digital conversion means for converting electrical signals from analog signals to digital signals; and, logic means for converting said digital signal into two 8 bit digital words for transmission through said sensor UART back to said satellite means.

3. The system of claim 2 further comprising:
a zero adjustment means for setting said sensor elements to a zero value.

4. The system of claim 3 wherein said satellite means comprises:
a satellite UART for communicating to and from said sensor means;
address decoding and control logic means being connected to said satellite UART;
microprocessor means connected to said address decoding and control logic means;
active RAM storage means connected to said address decoding and control logic means; and,
programmable read only memory means (PROM) connected to said sensor UART and to said address decoding and control logic means.

5. The system of claim 4 further including:
time out means for indicating a malfunctioning sensor means,
wherein said time out means will indicate a sensor malfunction if a given sensor does not respond to its address from said satellite means within a given predetermined period of time.

6. The system of claim 5 further including:
a power failure memory check means including a timing element for saving memory in case of a power failure,
wherein said check means adds up all of the memory in RAM upon the identification of a power failure and compares the pre failure number with the post failure RAM memory to determine if memory has been lost during the power failure interval.

7. The system of claim 6 wherein said timing element is a monostable multivibrator.

8. The system of claim 7 wherein said valve means comprise solenoid valves and a plurality of sensor means are fed zero and span gas by no more than two solenoid valves respectively.

9. A gas sensing system comprising:
a satellite means including a central processing unit (CPU) means for controlling said system and for transmitting information in a digital code having a predetermined number of bits;
a single pair of information leads;
sensor means for sensing a gas attached to said satellite means by said single pair of information leads;
a source of zero calibration gas;
a source of span gas;
valve means for applying said zero calibration gas and said span gas to said sensor means;
a master controller means for controlling a plurality of satellite means; and,
a parity determining means within said sensor means for generating a digital word in response to interrogation from said satellite means which differs by one parity bit from the digital word generated by said satellite means so that said satellite means can recognize that it is getting a response from the addressed sensor means and so that the non-addressed sensor means recognizes that the digital word is not coming from said satellite means,
wherein said satellite means communicates to said sensor means and said sensor means communicates with said satellite means exclusively on said single pair of information leads and further wherein application of said zero calibration gas sets a zero point for said sensor means and application of said span gas sets an intermediate range point for said sensor means whereby said CPU takes both said zero point and said intermediate range point and extrapolates the actual value of subsequent gas measurements from said two points.

10. A gas sensing system comprising:
a satellite means including a central processing unit (CPU) means for controlling said system and for transmitting information in a digital code having a predetermined number of bits;
a single pair of information leads;
sensor means for sensing a gas attached to said satellite means by said single pair of information leads; and,
a parity determining means within said sensor means for generating a digital word in response to interrogation from said satellite means which differs by one parity bit from the digital word generated by said satellite means so that said satellite means can recognize that it is getting a response from the addressed sensor means and so that the non-addressed sensor means recognizes that the digital word is not coming from said satellite means,
wherein said satellite means communicates to said sensor means and said sensor means communicates with said satellite means exclusively on said single pair of information leads.

11. The system of claim 10 further comprising:
a master controller means for controlling a plurality of satellite means.

* * * * *